US011175252B2

(12) United States Patent
Suster et al.

(10) Patent No.: US 11,175,252 B2
(45) Date of Patent: Nov. 16, 2021

(54) DIELECTRIC SENSING FOR BLOOD CHARACTERIZATION

(71) Applicant: CASE WESTERN RESERVE UNIVERSITY, Cleveland, OH (US)

(72) Inventors: Michael Suster, Cleveland Heights, OH (US); Pedram Mohseni, Highland Heights, OH (US); Debnath Maji, Cleveland, OH (US); Umut Gurkan, Shaker Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 479 days.

(21) Appl. No.: 16/254,446

(22) Filed: Jan. 22, 2019

(65) Prior Publication Data

US 2019/0154603 A1   May 23, 2019

Related U.S. Application Data

(63) Continuation-in-part of application No. 16/070,126, filed as application No. PCT/US2017/013797 on Jan. 17, 2017, now Pat. No. 10,674,931.

(Continued)

(51) Int. Cl.
*G01N 27/02* (2006.01)
*G01N 27/22* (2006.01)
(Continued)

(52) U.S. Cl.
CPC ......... *G01N 27/026* (2013.01); *A61B 5/0507* (2013.01); *A61B 5/0537* (2013.01);
(Continued)

(58) Field of Classification Search
None
See application file for complete search history.

(56) References Cited

U.S. PATENT DOCUMENTS 558,086 A   4/1896   Lyon
4,686,857 A   8/1987   Kato
(Continued)

FOREIGN PATENT DOCUMENTS

CN   101720432 A   6/2010
CN   102680523 A   9/2012
(Continued)

OTHER PUBLICATIONS

Extended European Search Report for Application No. 17739159.6, dated Aug. 2, 2019.
(Continued)

*Primary Examiner* — Jas A Sanghera
(74) *Attorney, Agent, or Firm* — Tarolli, Sundheim, Covell & Tummino LLP

(57) ABSTRACT

As one example, a fluid monitoring apparatus includes a dielectric microsensor that includes a capacitive sensing structure integrated into a microfluidic channel. The microfluidic channel includes a fluid input to receive a sample volume of a sample under test (SUT). A transmitter provides an input radio frequency (RF) signal to an RF input of the microsensor. A receiver receives an output RF signal from the microsensor. A computing device computes dielectric permittivity values of the SUT that vary over a time interval based on the output RF signal. The computing device may determine an indication of platelet count based on the computed dielectric permittivity values over at least a portion of the time interval.

20 Claims, 10 Drawing Sheets

Related U.S. Application Data

(60) Provisional application No. 62/745,852, filed on Oct. 15, 2018, provisional application No. 62/279,467, filed on Jan. 15, 2016.

(51) Int. Cl.

| | |
|---|---|
| G01N 33/49 | (2006.01) |
| A61B 5/0507 | (2021.01) |
| A61B 5/145 | (2006.01) |
| A61B 5/0537 | (2021.01) |
| G01N 27/08 | (2006.01) |
| A61B 5/05 | (2021.01) |

(52) U.S. Cl.
CPC ........... *A61B 5/145* (2013.01); *G01N 27/221* (2013.01); *G01N 33/4905* (2013.01); *A61B 5/05* (2013.01); *G01N 27/08* (2013.01)

(56) References Cited

U.S. PATENT DOCUMENTS

| | | | |
|---|---|---|---|
| 4,884,457 | A | 12/1989 | Hatton |
| 5,042,299 | A | 8/1991 | Wells |
| 6,255,954 | B1 | 7/2001 | Brown et al. |
| 6,362,632 | B1 | 3/2002 | Livingston |
| 6,467,358 | B1 | 10/2002 | Nishi et al. |
| 6,922,064 | B2 | 7/2005 | Halalay et al. |
| 7,541,004 | B2 | 6/2009 | Niksa et al. |
| 8,735,163 | B2 | 5/2014 | Hayahi et al. |
| 8,776,246 | B2 | 7/2014 | Allegri et al. |
| 8,884,771 | B2 | 11/2014 | Cooke et al. |
| 9,194,859 | B2 | 11/2015 | Emeric et al. |
| 2003/0090276 | A1 | 5/2003 | Weide et al. |
| 2004/0147032 | A1 | 7/2004 | Martin et al. |
| 2004/0237657 | A1 | 12/2004 | Xie et al. |
| 2010/0235107 | A1 | 9/2010 | Fukumura et al. |
| 2010/0251816 | A1 | 10/2010 | Bahorich et al. |
| 2010/0252452 | A1 | 10/2010 | Newman et al. |
| 2011/0234240 | A1 | 9/2011 | Yager |
| 2012/0055810 | A1 | 3/2012 | Zhou |
| 2012/0112850 | A1 | 5/2012 | Kim et al. |
| 2012/0238026 | A1 | 9/2012 | Hayashi et al. |
| 2013/0204202 | A1 | 8/2013 | Trombly et al. |
| 2013/0296847 | A1 | 11/2013 | Germain et al. |
| 2014/0114592 | A1 | 4/2014 | Eilertsen |
| 2015/0346125 | A1 | 12/2015 | Hayashi et al. |
| 2015/0346131 | A1* | 12/2015 | Mohseni ............... G01N 27/026 324/663 |
| 2016/0011170 | A1 | 1/2016 | Brun et al. |

FOREIGN PATENT DOCUMENTS

| | | |
|---|---|---|
| EP | 2 375 244 A1 | 10/2011 |
| JP | 2012194087 A | 10/2012 |
| WO | 2010109317 A1 | 9/2010 |
| WO | 2014/141845 A1 | 9/2014 |
| WO | 2016/040490 A1 | 3/2016 |

OTHER PUBLICATIONS

Maji Debnath et al., "Monitoring time course of human whole blood coagulation using a microfluidic dielectric sensor with a 3D capacitive structure", Aug. 25, 2015, pp. 5904-5907.

Yoshihito Hayashi et al., "Principles of Dielectric Blood Coagulometry as a Comprehensive Coagulation Test", Analytical Chemistry, vol. 87, No. 19, Sep. 14, 2015.

Supplementary European Search Report for Application No. 17739159.6, dated Aug. 21, 2019.

Ahmed A. Helmy, et al., "A 1-8-GHz Miniaturized Spectroscopy System for Permittivity Detection and Mixture Characterization of Organic Chemicals", IEEE Transactions on Microwave Theory and Techniques, vol. 60, No. 12, Dec. 2012, pp. 4157-4170.

Ahmed A. Helmy, et al., "A Self-Sustained CMOS Microwave Chemical Sensor Using a Frequency Synthesizer", IEEE Journal of Solid-State Circuits, vol. 47, No. 10, Oct. 2012, pp. 2467-2483.

Ahmed A. Helmy, et al., "Complex Permittivity Detection of Organic Chemicals and Mixtures Using a 0.5-3-GHz Miniaturized Spectroscopy System", IEEE Transactions on Microwave Theory and Techniques, vol. 61, No. 12, Dec. 2013, pp. 4646-4659.

Ahmet C. Sabuncu, et al., "Microfluidic impedance spectroscopy as a tool for quantitative biology and biotechnology", Biomicrofluidics 6, 034103 (2012).

Arun Manickam, et al., "A CMOS Electrochemical Impedance Spectroscopy (EIS) Biosensor Array", IEEE Transactions on Biomedical Circuits and Systems, vol. 4, No. 6, Dec. 2010, pp. 379-390.

Chao Yang, et al., "Compact Low-Power Impedance-to-Digital Converter for Sensor Array Microsystems", IEEE Journal of Solid-State Circuits, vol. 44, No. 10, Oct. 2009, pp. 2844-2855.

Ebrahim Ghafar-Zadeh, et al., "A Hybrid Microfluidic/CMOS Capacitive Sensor Dedicated to Lab-on-Chip Applications", IEEE Transactions on Biomedical Circuits and Systems, vol. 1, No. 4, Dec. 2007, pp. 270-277.

G. R. Facer, et al., "Dielectric spectroscopy for bioanalysis: From 40 Hz to 26.5 GHz in a microfabricated wave guide", Applied Physics Letters, vol. 78, No. 7, Feb. 12, 2001, pp. 996-998.

Hamed Mazhab-Jafari,et al., "16-Channel CMOS Impedance Spectroscopy DNA Analyzer With Dual-Slope Multiplying ADCs", IEEE Transactions on Biomedical Circuits and Systems, vol. 6, No. 5, Oct. 2012, pp. 468-478.

James C. Booth, et al., "Quantitative Permittivity Measurements of Nanoliter Liquid Volumes in Microfluidic Channels to 40 GHz", IEEE Transactions on Instrumentation and Measurement, vol. 59, No. 12, Dec. 2010, pp. 3279-3288.

Jun-Chau Chien, et al., "A 1-50 GHz Dielectric Spectroscopy Biosensor with Integrated Receiver Front-end in 55nm CMOS", 2013.

Jun-Chau Chien, et al., "A 6.S/11117.S/30-GHz High Throughput Interferometer-based Reactance Sensors using Injection-Locked Oscillators and Ping-Pong Nested Chopping", 2014 Symposium on VLSI Circuits Digest of Technical Papers.

Kang-Ho Lee, et al., "A CMOS Impedance Cytometer for 3D Flowing Single-Cell Real-Time Analysis ?S with Error Correction", 2012 IEEE International Solid-State Circuits Conference, pp. 304-306.

Katia Grenier, et al., "Integrated Broadband Microwave and Microfluidic Sensor Dedicated to Bioengineering", IEEE Transactions on Microwave Theory and Techniques, vol. 57, No. 12, Dec. 2009, pp. 3246-3253.

Khalil Heileman, et al., "Dielectric spectroscopy as a viable biosensing tool for cell and tissue characterization and analysis", Biosensors and Bioelectronics, 49 (2013), pp. 348-359.

Masoud Moslehi Bajestan, et al., "A 0.62-1 OGHz CMOS Dielectric Spectroscopy System for Chemical/Biological Material Characterization", 2014.

Mehran Bakhshiani, et al., "A 9 MHz-2.4 GHz Fully Integrated Transceiver IC for a Microfluidic-CMOS Platform Dedicated to Miniaturized Dielectric Spectroscopy", IEEE Transactions on Biomedical Circuits and Systems, vol. 9, No. 6, Dec. 2015, pp. 849-861.

Mehran Bakhshiani, et al., "A Broadband Sensor Interface IC for Miniaturized Dielectric Spectroscopy From MHz to GHz", IEEE Journal of Solid-State Circuits, vol. 49, No. 8, Aug. 2014.

Mehran Bakhshiani, et al., "A Microfluidic-CMOS Platform with 3D Capacitive Sensor and Fully Integrated Transceiver IC for Palmtop Dielectric Spectroscopy", 2015 IEEE International Solid-State Circuits Conference, pp. 386-388.

Michael A. Suster, et al., "A Circuit Model of Human Whole Blood in a Microfluidic Dielectric Sensor", IEEE Transactions on Circuits and Systems—II: Express Briefs, vol. 63, No. 12, Dec. 2016, pp. 1156-1160.

Michael A. Suster, et al., "An RF/Microwave Microfluidic Sensor Based on a 3D Capacitive Structure with a Floating Electrode for Miniaturized Dielectric Spectroscopy", 2014.

Michael A. Suster, et al., "An RF/Microwave Microfluidic Sensor Based on a Center-Gapped Microstrip Line for Miniaturized Dielectric Spectroscopy", 2013.

(56) References Cited

OTHER PUBLICATIONS

Michael A. Suster, et al., "An RF/Microwave Microfluidic Sensor for Miniaturized Dielectric Spectroscopy Based on Sensor Transmission Characteristics", 2015.
Milan Daphtary, et al., "Broadband Capacitive Sensor CMOS Interface Circuit for Dielectric Spectroscopy", ISCAS 2006, pp. 4285-4288.
Osama Elhadidy, et al., "A CMOS Fractional-PLL-Based Microwave Chemical Sensor With 1.5% Permittivity Accuracy" IEEE Transactions on Microwave Theory and Techniques, vol. 61, No. 9, Sep. 2013, pp. 3402-3416.
Osama Elhadidy, et al., "A Wide-Band Fully-Integrated CMOS Ring-Oscillator PLL-Based Complex Dielectric Spectroscopy System", IEEE Transactions on Circuits and Systems—I: Regular Papers, vol. 62, No. 8, Aug. 2015, pp. 1940-1949.
S S Stuchly, et al., "Microwave coplanar sensors for dielectric measurements", Meas. Sci. Technol. 9 (1998) pp. 1324-1329.
S. Gawad, et al., "Micromachined impedance spectroscopy flow cytometer for cell analysis and particle sizing", Lab on a Chip, 2001, 1, pp. 76-82.
Sanghyun Seo, et al., "High Frequency Wideband Permittivity Measurements of Biological Substances Using Coplanar Waveguides and Application to Cell Suspensions", 2008, pp. 915-918.
Mohseni, et al., "A Miniaturized Dielectric Blood Coagulometer"; Oct. 20, 2015.
Applicant: Case Western Reserve University; Japanese Patent Application No. 2018-536778, Filed Jan. 17, 2017; Entitled "Dielectric Sensing for Sample Characterization"; Japanese OA; Nov. 27, 2020.
Applicant: University of Case Western Reserve; "Dielectric Sensing for Sample Characterization"; Chinese Office Action; dated Mar. 8, 2021; 8 pgs.
Applicant: Case Western Reserve University; European Patent Application No. EP17739159.6; European Office Action dated Apr. 30, 2021; 6 pgs.

* cited by examiner

DIELECTRIC SENSING FOR BLOOD CHARACTERIZATION

CROSS REFERENCE TO RELATED APPLICATION

This application claims the benefit of priority from U.S. Provisional Application No. 62/745,852, filed Oct. 15, 2018, and entitled DIELECTRIC SENSING FOR BLOOD CHARACTERIZATION, and is also a continuation-in-part of U.S. patent application Ser. No. 16/070,126, filed Jul. 13, 2018, and entitled DIELECTRIC SENSING FOR SAMPLE CHARACTERIZATION, which is a 371 of International Application No. PCT/US2017/13797, which claims the benefit of U.S. Provisional Patent Application No. 62/279,467, filed Jan. 15, 2016, and entitled SENSOR, APPARATUS, SYSTEMS AND METHODS OF MAKING SAME. Each of the above-identified applications is incorporated herein by reference in its entirety.

TECHNICAL FIELD

This disclosure relates to dielectric sensing to determine properties of a sample.

BACKGROUND

Quantitative measurement of the complex dielectric permittivity of a material versus frequency (e.g., dielectric spectroscopy, also known as DS) can be a powerful monitoring technique with a broad range of applications. For example, DS can be utilized for chemical analysis of oil in the petroleum industry, analysis of substances for security or defense purposes, soil moisture monitoring in agriculture, fermentation monitoring during the production of alcoholic beverages, food quality/safety monitoring and drug development in the pharmaceutical industry. DS can also be used as an analytical tool in the biomedical field as a label-free, non-destructive and real-time method to study the interaction of RF/microwave fields with biological/biochemical samples with minimal sample preparation. Key molecular characteristics of biomaterials such as human blood, spinal fluid, breast tissue and skin have been studied using DS for applications in disease detection and clinical diagnosis. Typical DS systems tend to be large and expensive, making them cost-prohibitive in certain circumstances.

SUMMARY

This disclosure relates to sensor systems and methods to characterize properties of a blood sample.

As one example, a monitoring apparatus includes a dielectric microsensor comprising a capacitive sensing structure integrated into a microfluidic chamber, the microfluidic chamber including a fluid input to receive a volume of a blood sample. A transmitter is to provide an input radio frequency (RF) signal to an RF input of the dielectric microsensor. A receiver is to receive an output RF signal from an RF output of the dielectric microsensor. A computing device computes dielectric permittivity values of the blood sample that vary over a time interval based on the output RF signal. The computing device is to determine an indication of platelet count for the blood sample based on the dielectric permittivity values computed over at least a portion of the time interval.

As another example, a method includes providing an input radio frequency (RF) signal to a dielectric microsensor. The method also includes receiving an output RF signal from the dielectric microsensor in response to the input RF signal, the RF output signal representing a measure of impedance of a blood sample disposed in the dielectric microsensor. The method also includes calculating dielectric permittivity values of the blood sample over a measurement time interval based on the output RF signal. The method also includes analyzing the dielectric permittivity values of the blood sample over at least a portion of the measurement time interval to determine an indication of platelet count for the blood sample.

A system includes a sensor interface comprising an input and an output, the output to connect to an input of a sensing apparatus and the input to connect to an output of the sensing apparatus, the sensing apparatus to receive a blood sample. A transmitter is to provide an input radio frequency (RF) signal to the output of the sensor interface. A receiver is to receive an output RF signal from the input of the sensor interface in response to the input RF signal and based on an impedance of the sensor apparatus. The system also includes a computing device to compute dielectric permittivity values of the blood sample that vary over a time interval based on the output RF signal, the computing device to determine an indication of platelet count for the blood sample based on the dielectric permittivity values computed over at least a portion of the time interval.

DETAILED DESCRIPTION

This disclosure relates to dielectric sensing to determine properties of a sample, such as blood sample. For example, a dielectric microsensor, associated interface electronics and computing device can be integrated in a portable apparatus (e.g., a handheld or desktop unit). The microsensor can be placed within a chamber defined by a microfluidic channel to measure impedance characteristics of a sample under test (SUT) (e.g., a liquid, solution or a gas) in the channel. The measured impedance can be used to compute corresponding dielectric permittivity values for the SUT over time during a measurement time interval. The time-based dielectric permittivity values are analyzed to determine permittivity parameters that correlate to one or more properties of the SUT. Examples of permittivity parameters for a given SUT include a time to peak dielectric permittivity, a difference between peak and plateau permittivity values, rate of change (e.g., slope) in permittivity values associated with a portion of a time interval, as well as other functional characterizations of the dielectric permittivity values. In some examples, a disposable dielectric microsensor can be removably connected, such that the same monitoring apparatus can be reused for taking measurements for numerous different SUTs.

As an example where blood is used as the SUT, the dielectric permittivity values can be analyzed to determine one or more dielectric parameters that provide an indication of platelet count. Other hemostatic properties, such as platelet function and/or anticoagulation property of the blood SUT may also be determined based on analysis of the dielectric permittivity values. These and other properties thus can be evaluated to determine quantitative platelet defects and identify potential thrombotic complications. The apparatuses, systems and methods disclosed herein enables rapid, high-throughput, low-cost DS measurements that enables rapid and comprehensive diagnosis of platelet and coagulation defects, which can be utilized at the point-of-care. For example, the approach may be implemented as a low-cost, easy-to-use, and portable platform for assessment of platelet count-induced changes in the hemostatic process.

Figure 1:
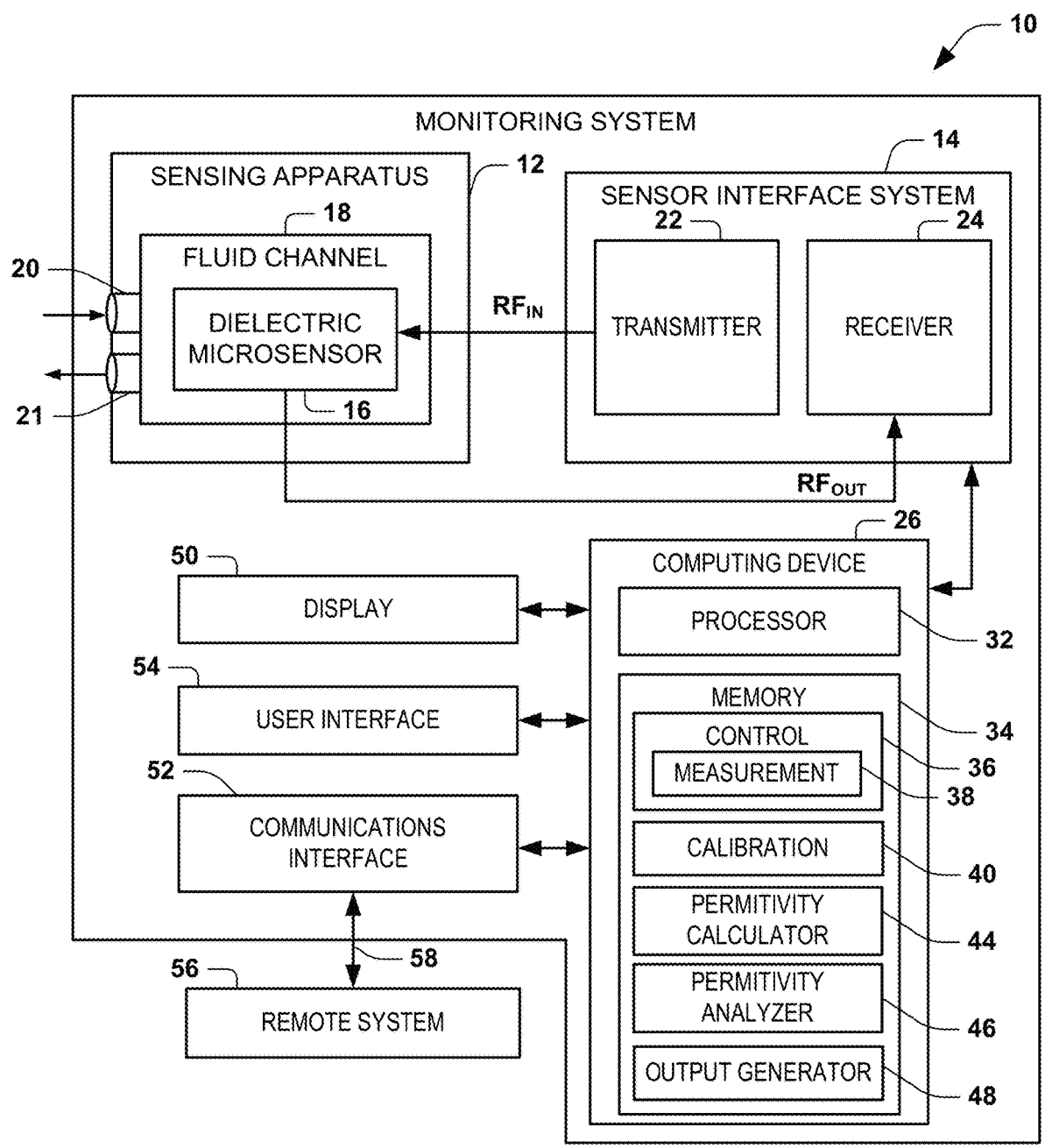
FIG. 1 depicts an example of a sample monitoring apparatus.

FIG. 1 depicts an example of a system 10 to determine properties of a sample under test (SUT) based on dielectric permittivity measurements of the sample. The system 10 can include a sensing apparatus 12 and a sensor interface system 14. The sensor interface system 14 can drive a dielectric sensor 16 with an RF input signal ($RF_{IN}$). For example, the dielectric sensor 16 is a dielectric spectroscopy (DS) microsensor that includes circuitry (e.g., an arrangement of electrodes) residing in a fluid channel 18 to measure impedance of the microsensor. The dielectric sensor 16 is configured to have a dielectric permittivity that corresponds to its measured impedance and which depends on the SUT that is placed in the fluid channel 18. For example, a fluid SUT can be provided (e.g., from a source of fluid, such as a micropipette) into the fluid channel 18 via one or more fluid ports 20. In some examples, the fluid SUT can be substantially still within the channel 18 or, in other examples it can be flowing through the channel during measurements. The fluid channel 18 can be a microfluidic chamber having a volume that is less than about 10 µL, for example.

As an example, the dielectric sensor 16 can include electrodes distributed in the channel 18 in an opposing and spaced apart relationship as to provide a capacitive sensing area between opposing surfaces of the spaced apart electrodes. For instance, a floating electrode can be fixed with respect to a given surface of the fluid channel in a spaced apart opposing relationship from a pair of sensing electrodes fixed with respect to another surface of the channel. The pair of sensing electrodes thus can be substantially coplanar along a given surface of the fluid channel 18 that opposes and is parallel to the surface of the floating electrode. One of the sensing electrodes can be configured to receive the RF input signal ($RF_{IN}$) as an excitation signal from the sensor interface system 14 and the other sensing electrode can provide a corresponding RF output signal ($RF_{OUT}$) to the sensor interface system.

The sensor interface system 14 includes a transmitter 22 and a receiver 24 (e.g., may be integrated into a transceiver). The transmitter 22 can be configured to provide the RF input signal at a desired excitation frequency. The excitation frequency, for example, can be in the microwave range. For instance, the transmitter 22 can provide the RF input signal that sweeps through a range of frequencies, such as from about 1 KHz to about 100 GHz (e.g., from about 1 KHz to about 100 MHz). The frequency range may be a continuous range through which the excitation is swept. In other examples, the transmitter 22 can provide $RF_{IN}$ at a plurality of different discrete excitation frequencies, which can be set according to the SUT and application requirements. As one example, for monitoring blood SUT's, the transmitter 22 can provide $RF_{IN}$ to include at least frequencies at about 1 MHz and also at about 100 MHz. The excitation frequency(ies) can be set in response to a program input signal (e.g., via user interface 54 of the apparatus or sent from a remote system 56), such as to adjust the frequency according to application requirements to maximize sensitivity of the sensor. The frequency range for the excitation signal can be continuous across the range or be provided in two or more discrete frequency bands, which can be user programmable (e.g., in response to a user input).

The receiver 24 is configured to provide an output signal (OUT) representing measured sensor transmission characteristics based on the RF output signal from the dielectric sensor 16 implemented in the sensing apparatus 12. The output signal can be an analog signal or be converted to a digital signal (e.g., via an analog-to-digital converter). The receiver 24 can include circuitry configured to process the RF output signal, such as by amplifying (e.g., variable gain) and filtering the RF output signal to ascertain complex signal components of $RF_{OUT}$, which filtering can be configured according to the frequency or frequency range of the excitation signal $RF_{IN}$. The RF output signal can be a complex signal corresponding to voltage transmission measurements through the dielectric sensor 16, which varies as a function of the complex impedance or admittance as seen at an output node thereof (e.g., demonstrated at $RF_{OUT}$ in various figures herein). That is, $RF_{OUT}$ can have a predetermined relationship with respect to a change in dielectric permittivity caused by the SUT (e.g., blood) within the channel 18.

The transmitter 22 and receiver 24 can be implemented in an integrated circuit chip (e.g., system on chip) or they could be implemented as separate components configured to perform the functions disclosed herein. While the transmitter 22 and receiver 24 are demonstrated in FIG. 1 as co-residing in the interface system 14 (e.g., in a single IC chip), in other examples, the transmitter and receiver could be implemented as independent separate circuits.

In the example of FIG. 1, the sensor system 10 also includes a computing device 26. The computing device 26 can include a processor (e.g., having one or more processor cores) 32 and memory 34. The memory 34 can store instructions and data, and the processor 32 can access the memory to execute the instructions based on the stored data to perform functions and methods disclosed herein.

For example, the memory 34 stores control functions 36, which when executed by the processor 28, control operation of the sensor interface system 14. For example, the DS control 32 can selectively control the range of frequencies (e.g., frequency bands) of an RF output signal applied by the transmitter 22 to each respective DS sensor 16. The control 36 also includes instructions executable by processor 32 to perform measurement functions 38 based on the output from the receiver.

As an example, the measurement function 38 is configured to measure complex impedance based upon amplitude and phase provided in the output signal $RF_{OUT}$. For instance, the measurement function 38 cooperates with the sensor interface system 14 to operate as an impedance analyzer. In this way, the measurement function 38 measures the complex impedance, corresponding to the capacitance of the dielectric sensor 16 based on the SUT disposed within the fluid channel 18 in response to the input excitation signal $RF_{IN}$. As mentioned, the transmitter 22 can provide $RF_{IN}$ as an excitation signal at one or more discrete frequencies or sweep across one or more predefined frequency bands. The measurement function 38 thus stores impedance (e.g., capacitance) measurement values and associated timestamps (e.g., a time index) as time-based impedance data in the memory 34 based on the RF output signal from the sensor 16. Additional information (e.g., metadata) may also be stored in the impedance data, such as to specify the input signal frequency, temperature and/or other parameters associated with the SUT.

By way of further example, during the first portion of a test phase, control 36 can control the transmitter 22 to provide the RF input signal within a first range of frequencies (e.g., a low frequency range). During one or more subsequent or other different phases of the sensing process, control 36 can control the transmitter 22 to provide the RF input signal for one or more different range of frequencies for exciting the sensor and the associated SUT disposed in the fluid channel 18. For example, different frequencies may be used to extract different properties of the SUT. The receiver 24 thus can receive and provide corresponding output signals associated with each phase of the sensing process. The control 36 can also control the receiver 24 to provide the RF output data as a DC output voltage in the I-mode and another DC output voltage in the Q-mode. While the control and measurement functions 36 and 38 have been described as being part of the computing device 26, in other examples, the measurement and control functions could be distributed between the sensor interface system 14 and the computing device or be implemented separately from the computing device (e.g., as part of the sensor interface or as a separate control system.

The computing device 26 further can include data processing methods and/or functions 36, 44 and 46 for computing permittivity based on the output data provided by the measurement function 38 for a given measurement interval. Thus, the computing device 26 further can process the received input signals from a given sensor (or from multiple sensors) and provide output data that includes the impedance measurements as well as permittivity data and other information derived from the measurements to representing complex permittivity, raw data corresponding to the measurements RF output signal as well as other information derived therefrom.

As a further example, the computing device 26 includes a calibration function 40 programmed to determine a calibration permittivity for a given sensor 16. For example, the control function 36 can control transmitter to provide $RF_{IN}$ that is at or includes a predetermined excitation frequency (or frequency band) in which two or more substantially different SUTs are known to have little or no difference in permittivity. Thus, different types of samples may utilize different excitation frequencies for calibration as well as for testing depending on the samples. For the example of a blood SUT, the calibration input frequency can be about 100 MHz. In this way, the measured impedance (e.g., capacitance) corresponds to the capacitance of water, and the resulting permittivity derived (e.g., by permittivity calculator 44) from $RF_{OUT}$ in response to $RF_{IN}$ at the calibration frequency provides a measure of water permittivity for the sensor 16. That is, the calibration capacitance and permittivity represent the capacitance and permittivity of the sensor 16 with an SUT in the channel 18 with a known permittivity value (e.g., water has a known permittivity of approximately 80 at 100 MHz). This calibration measurement of impedance (e.g., by measurement function 38) and determination of the calibration permittivity (e.g., by permittivity calculator 44) may be implemented as part of the normal sensing process while an SUT is within the fluid channel 18, such as described above, so long as the excitation is provided at an appropriate calibration frequency.

By way further example, if the sensor apparatus 12 is being used to measure the permittivity of blood, at 100 MHz, the permittivity of blood is close to that of water, (e.g., $\varepsilon_{r,blood}(@100\ MHz) \cong \varepsilon_{r,water}(@100\ MHz) \cong 80$). This relationship and calibration frequency thus may be used for water-based substances other than blood. In particular, this relationship can be used to implement a simplified calibration procedure for blood that can be implemented while the blood SUT remains in the sensing apparatus. Other relationships and different calibration frequencies may be determined and used for other types of SUTs in a like procedure.

In the example to determine the permittivity of blood at 1 MHz, the following procedure may be used. After the sensing apparatus is attached to the system 10, blood may be inserted into the sensor (e.g., using a micropipette). The admittance for blood (i.e., $Y_{s,blood}$) is measured over multiple frequencies (e.g., sweep 1 kHz to 100 MHz, or at 1 MHz and 100 MHz), as disclosed herein.

The nominal capacitance for the sensor in the absence of an SUT (i.e., air-gap capacitance or $C_0$) is calculated, such as follows:

$$C_0 = \frac{Y_{s,blood}(@100\ MHz)}{j \times \omega \times \varepsilon_{r,blood}(@100\ MHz)},$$

where $\varepsilon_{r,blood}$ (@ 100 MHz) is taken as $\varepsilon_{r,blood}(@100\ MHz) \cong \varepsilon_{r,water}(@100\ MHz) \cong 80$.

The permittivity calculator 44 then computes the permittivity of blood at the frequency of interest (e.g., $\varepsilon_{r,blood}$ (@1 MHz)) such as follows:

$$\varepsilon_{r,blood}(@1\ MHz) = \frac{Y_{s,blood}(@1\ MHz)}{j \times \omega \times C_0},$$

where $C_0$ was calculated above based on the measured admittance of blood at the calibration frequency (e.g., 100 MHz).

Alternatively, the calibration measurement can be performed as a separate process for each SUT, such as before any SUT is placed in the fluid channel 18. The calibration function 42 stores the calibration permittivity value (e.g., corresponding to the air gap permittivity or capacitance) in the memory 34. In some types of sensing, such as for $T_{PEAK}$, calibration function 40 may be omitted since the time to peak for a given type of material is not affected by calibrating or not calibrating permittivity of the sensor.

The permittivity calculator 44 is also executed by the processor 32 to determine dielectric permittivity of the SUT. This may include for determining the calibration permittivity as mentioned above, as well as more generally during sensing. The permittivity calculator 44 thus determines the dielectric permittivity for the dielectric sensor 16 and the SUT over a corresponding measurement time interval. This interval can range from the time in which the control 36 activates the sensor interface 14 to provide the RF input signal until a subsequent time in which the control 42 deactivates the sensor interface 14 when sensing is complete. The measurement interval may be a fixed time or it can be controlled and terminated based on monitoring the measured capacitance or determined permittivity.

As an example, the permittivity calculator 44 can determine a relative permittivity of the SUT based on a measured impedance at one or more measurement frequencies (e.g., one or more frequency bands) and based on the calibration permittivity (e.g., determined by calibration function 42). For example, the permittivity calculator 44 can compute the permittivity at a given time index and input frequency by dividing the measured impedance value (e.g., capacitance) by the calibration capacitance value (e.g., air gap capacitance) to provide a relative permittivity value for the SUT at the given time index. Additionally, in some examples, the permittivity values over the measurement interval may be normalized with respect to the permittivity at the first measurement point, peak permittivity or another value. The normalized, relative permittivity value can be computed for each of the plurality of measurement data points over a range of time indices that define the measurement time interval. Each permittivity value can be stored as permittivity data in the memory 34 for further processing and analysis. As mentioned, in some measurements (e.g., time-to-peak), calibration may be omitted and the permittivity calculator 44 can determine a permittivity of the SUT in the absence of the calibration permittivity and, in some cases without normalization.

The processor 32 can also execute a permittivity analyzer 46 that is programmed to determine one or more permittivity parameters based upon the dielectric permittivity values computed by the permittivity calculator 44. The permittivity analyzer 46 can determine parameters for one or more different portions of the measurement time interval, including up to the entire interval. As one example, the permittivity analyzer 46 analyzes the stored dielectric permittivity values over a portion of the measurement time interval to determine a time that it takes to reach a peak dielectric permittivity value ($T_{PEAK}$). For instance, the permittivity analyzer 46 employs a peak detector function to ascertain the peak permittivity value, and the time interval (e.g., an elapsed time) to reach the peak dielectric permittivity thus can be stored in memory as $T_{PEAK}$ for the SUT. This time value $T_{PEAK}$ may be the time index associated with when the associated impedance measurement was made or it may be determined as the difference between the start time and the time when the measurement occurred to provide $T_{PEAK}$. For the example where the SUT is a blood SUT, the $T_{PEAK}$ value thus can provide an indication of an anticoagulation property of the blood sample. The $T_{PEAK}$ value can be stored in the memory 34.

As another example, the permittivity analyzer 46 can be programmed to analyze the stored dielectric permittivity values to determine a difference between the peak dielectric permittivity value ($@T_{PEAK}$) and a plateau permittivity value, which difference is referred to as $\Delta\varepsilon_{r,max}$. The plateau permittivity value can represent a permittivity value that remains substantially constant over time, such as at a tail end portion of the measurement time interval. As used herein, the term substantially constant is intended to refer to a sufficiently small rate of change from a given value over time (e.g., about ±5% or less). The permittivity analyzer 46 can determine the plateau permittivity value, for example, by determining that the time derivative of the permittivity values remains less than a predetermined value or is zero over a period of time. The difference between peak permittivity and plateau permittivity values ($\Delta\varepsilon_{r,max}$) can be used to provide an indication of additional properties associated with the SUT. For the example of a blood SUT, the difference between peak permittivity and plateau permittivity values can provide a quantitative measure of platelets (e.g., platelet count) for the blood SUT. The indication of platelet count may specify a quantity or range of platelets, such as a concentration per volume of blood. Thus, by monitoring the indication of platelet count, a caregiver can identify quantitative platelet defects and/or rapid platelet depletion to facilitate an intervention/treatment. Additionally or alternatively, the difference between peak and plateau permittivity values may provide a qualitative measure associated with platelet function (e.g., clot firmness or clot stability) for the blood SUT.

In yet another example, the permittivity analyzer 46 can evaluate the dielectric permittivity values for the SUT over a portion of a time interval to determine the rate of change in permittivity values, such as corresponding to a slope of a portion of a curve representing the dielectric permittivity values. For instance, the permittivity analyzer 46 can determine a rising edge slope between the beginning of the measurement interval and the peak dielectric value. The permittivity analyzer 46 also may compute a falling edge slope such as between the $T_{PEAK}$ value and the plateau dielectric permittivity value. Further analysis can be made with respect to the tail portion between the peak and the plateau dielectric values to provide an indication of other properties associated with the SUT.

In some examples, an output generator 48 can utilize the computed permittivity parameter $\Delta\varepsilon_{r,max}$ as a readout parameter that is used to present associated information on a corresponding display 50 of the apparatus 10. The output generator can provide the output as including a presentation on the display 50, such as a graphical and/or textual representation of one or more permittivity parameters. An audio output may also be provided based on the one or more permittivity parameters. For example, the output generator 48 can provide an indication of the difference between peak and plateau permittivity values to the display 50, such as may be the calculated permittivity difference value or a scaled version thereof (e.g., an index that maps to ranges of platelet count values).

Additionally, the output generator may use the $T_{PEAK}$ value to present associated information on a corresponding display 50 of the apparatus 10. For example, the output generator 48 can display time to peak value, $T_{PEAK}$, and/or a graphical output of a curve representing the permittivity values over the measurement interval or a portion thereof. The output generator 48 further may be programmed to provide an indication of slope of the permittivity curve to the display 50 associated with other corresponding properties of the SUT determined by the permittivity analyzer 46.

In some cases, the display 50 may also present comparative results, which are determined by the permittivity analyzer 46 based on comparing the current results relative to a known standard or to one or more previous results for the same patient or a patient population. For use as a patient or point-of-care apparatus, for example, a set of instructions can also be generated and provided as an output to the display 50. If the $T_{PEAK}$ value is outside of expected parameters, for example, the output generator 48 can also send an alert to the display 50 to inform the user to seek medical assistance and/or adjust a prescribed medication. Additionally or alternatively, if the difference between permittivity value at $T_{PEAK}$ and the plateau permittivity is outside of expected parameters, the output generator 48 can provide an alert to the display. Corresponding results, including raw data and/or other computed permittivity information and analysis results, further may be provided to the display 50.

As mentioned, the apparatus includes a user interface 54 to interact with the system 10. The user interface 54 may include a touch screen interface, a keypad, a keyboard, a mouse, voice interface and/or a combination thereof. As an example, a user can use the user interface 54 to acknowledge information that is presented on the display such as before, during and after a measurement interval for a given SUT. Additionally or alternatively, a user may employ the user interface 54 to input information about the user (e.g., health and/or demographic information) and/or environment conditions. The user interface 54 can be utilized to program/configure the apparatus 10 for one or more parts of a sensing process such as disclosed herein. For instance, the user interface 54 can be utilized to set a range of one or more frequencies, including one or more frequency bands, to utilize for the excitation signal during testing of the SUT. For example, in response to instructions entered via the user interface 54, the computing device 26 can employ control 36 to instruct the transmitter 22 to operate accordingly. The instructions can be stored in memory 34 or other memory (e.g., a program register) of the transmitter 22 to control the frequency of the excitation signal and duration thereof that is applied during a test process. Additionally or alternatively, the user interface 54 can also be utilized to control the information that is presented in the display 50 as well as to perform other post processing functions (e.g., reporting functions, recording user responses to questions, etc.) and data analysis.

In some examples, the computing device 26 employs the communications interface 52 to communicate with the remote system 56 via a communications link 58. The communication link 58 can be implemented to include one or more physical connections (e.g., an electrically conductive connection or optical fiber), one or more wireless links (e.g., implemented according to an 802.11x standard or other short-range wireless communication) or a network infrastructure that includes one or more physical and/or wireless communications links.

The remote system 56 can include a server, a general purpose computing device (e.g., notebook computer, laptop, desktop computer, workstation, smartphone or the like) and/or it can be a special purpose system configured to interact with one or more of the apparatuses 10 via the link 58. For instance, the computing device 26 employs the communications interface 52 to send the remote system 56 permittivity-related information based on measurement results for a given SUT. As another example, the remote system 56 may send program instructions to the apparatus to configure and/or update its operating program instructions. In an example where the remote system comprises a back office system of a healthcare provider, the computing device 26 may send a copy of the raw measurement data and/or the results determined by the permittivity analyzer 46 using a secure communications over the link 58 (e.g., HIPPA compliant communications). In such an example, the remote system 56 may communicate with a plurality of apparatuses.

As mentioned, such communications can include an alert issued in response to the analyzer 46 determining that one or more SUT properties is outside of expected parameters. In other examples, the remote system can perform such analysis and return an alert to the apparatus via the link. In response, the alert can be presented on the display to the user (e.g., a patient or care provider). Regardless of where the alert originates (e.g., generated by the apparatus or remote system 56) such alert can trigger a corresponding notification to be sent to alert to one or more individuals (e.g., health care professionals). The corresponding notification may be delivered to each such recipient via a communications protocol, such as email, SMS text message, pager, telephone call or the like.

Figure 2:
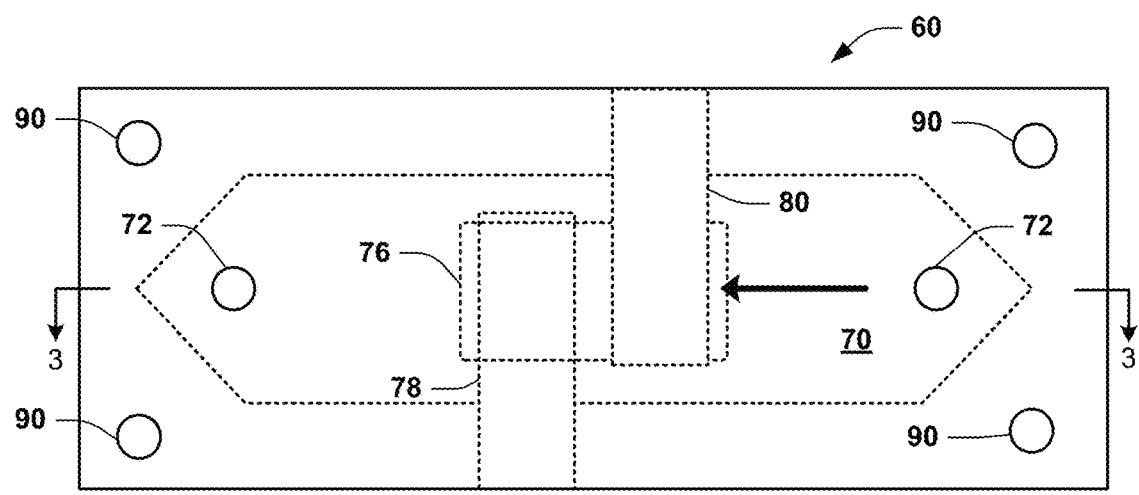
FIG. 2 depicts a top elevation of an example by dielectric microsensor.
Figure 3:
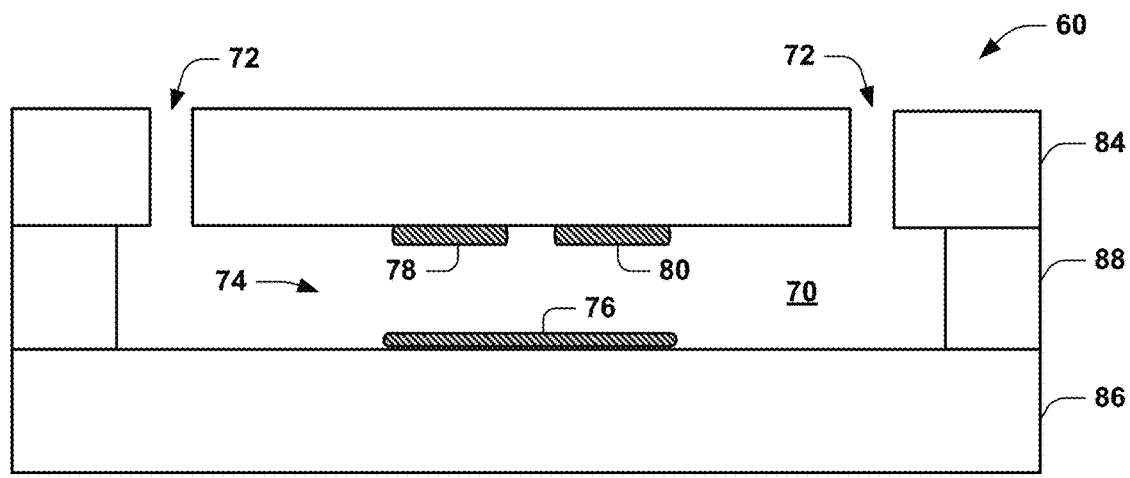
FIG. 3 depicts an example of the dielectric microsensor of FIG. 2 taken along the lines of 3-3.
Figure 4:
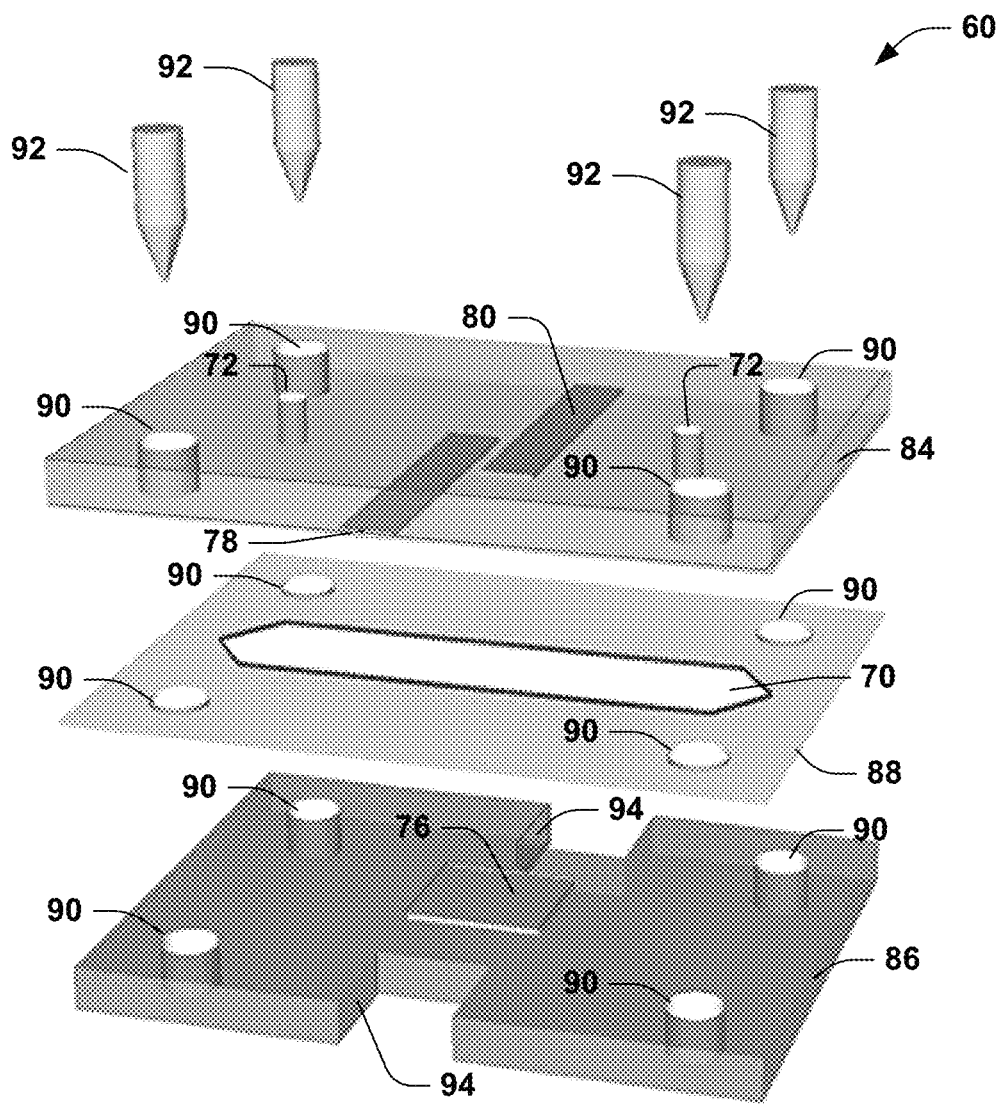
FIG. 4 is an assembly view of the example sensor of FIG. 2.

FIGS. 2, 3 and 4 demonstrate an example of a three-dimensional dielectric microsensor 60 (e.g., corresponding to the sensing apparatus 12). The microsensor 60 can be electrically coupled to a sensor interface system (e.g., interface 14), such as via electrical contacts. Other types of connections (e.g., electrically conductive or wireless) could also be utilized to provide for bi-directional communication with respect to the DS sensing apparatus 60.

In the example of FIGS. 2, 3 and 4, the interface system (e.g., transmitter 22) provides an RF input signal to an input 78 of the microsensor 60. The microsensor 60 includes circuitry having a complex admittance (e.g., capacitance) that varies as a function of dielectric permittivity of an SUT within a fluid channel 70, such as disclosed herein. The microsensor 60 includes an output 80 that provides an RF output signal to the interface system (e.g., interface 14) via an output connection (e.g., a pin or other type of electrical connection), which RF output signal varies as a function of time based on the input frequency and the dielectric permittivity of the SUT.

In the example of FIGS. 2, 3 and 4, the microsensor 60 includes a fluid channel 70 into which a volume of an SUT (e.g., liquid or gas) can be introduced via ports 72 (e.g., inlet and outlet holes). For purposes of clarity, the following discussion presumes that the SUT is a fluid, such as blood. Of course, other types of SUTs could be used in other examples.

The microsensor 60 includes a capacitive sensor 74 disposed within the fluid channel 70. For example, the capacitive sensor 74 includes a floating electrode 76 spaced apart from and opposing sensing electrodes 78 and 80 within the fluid channel 70 to provide a volumetric sensing area (e.g., corresponding to the area of overlap between the floating electrode and associated sensing electrodes). The capacitance of the sensor 74 is based on permittivity of material (or the absence) between electrodes 76, 78 and 80. The sensing electrodes 78 and 80 in the capacitive sensor 74 can be electrically isolated from each other. The RF input signal is coupled to the input sensing electrode 76 for excitation of the capacitive sensor 74 and the other sensing electrode 80 is coupled to provide $RF_{OUT}$.

As demonstrated in the cross-sectional view of FIG. 3, the sensor 74 includes planar sensing electrodes separated from a floating electrode through a microfluidic channel 70 to form a capacitive sensing area with nominal air-gap capacitance, $C_0$, which is defined by the overlapping electrode area and microfluidic channel height. For example, at the excitation frequency, co, the capacitive sensing area admittance is $Y_S = \omega C_0 \varepsilon_r'' + j\omega C_0 \varepsilon_r'$, when the channel is loaded with an SUT having a complex dielectric permittivity of $\varepsilon_r = \varepsilon_r' - j\varepsilon_r''$. In the example of FIGS. 2-4, the sensing structure is electrically connected to the output node, to provide an output signal $RF_{OUT}$ such as $V_{OUT} \propto V_{RF} \omega C_0 (\Delta \varepsilon_r'' + j\Delta \varepsilon_r')$ when the sensor is driven by the input signal RF/microwave signal ($V_{RF}$) and the fluid channel 70 is loaded with an SUT having $\Delta \varepsilon_r$.

As also demonstrated in the cross sectional view of FIG. 3 (and the assembly view of FIG. 4), the microsensor 60 can be fabricated in multiple parts that are attached together to provide a resultant sensor structure. As shown in FIG. 4, for example, the microsensor 60 includes a top part 84 and a bottom part 86 that is spaced apart from the top part by an intermediate channel layer 88. The bottom part 86 includes a floating electrode 76 fabricated on a surface of the substrate layer. Electrodes 78 and 80 are disposed on a corresponding surface of its substrate layer. In this example, the sensing electrodes 78 and 80 each extend from opposite side edges of the substrate beyond a central longitudinal axis of the microsensor 60 to terminate in respective ends near a central portion of the substrate. The middle part 88 has a thickness that determines a volume of the channel 70 formed therein. The top part 84 can include the inlet/outlet ports 72 to provide fluid communication for accessing the volume defined by the channel 70. For example, the channel 70 in part 88 and associated ports 72 can be fabricated by micromachining (e.g., laser micromachining) or by other types of machining or etching techniques. In some examples, the surface of channel 70 further can be coated with a polymer or other material (e.g., electrically insulating film, such as poly(ethylene glycol)) to help protect against protein adsorption onto the surfaces that contact the protein solutions. The polymer can be applied via physisorption or chemisorptions, for example.

Figure 5:
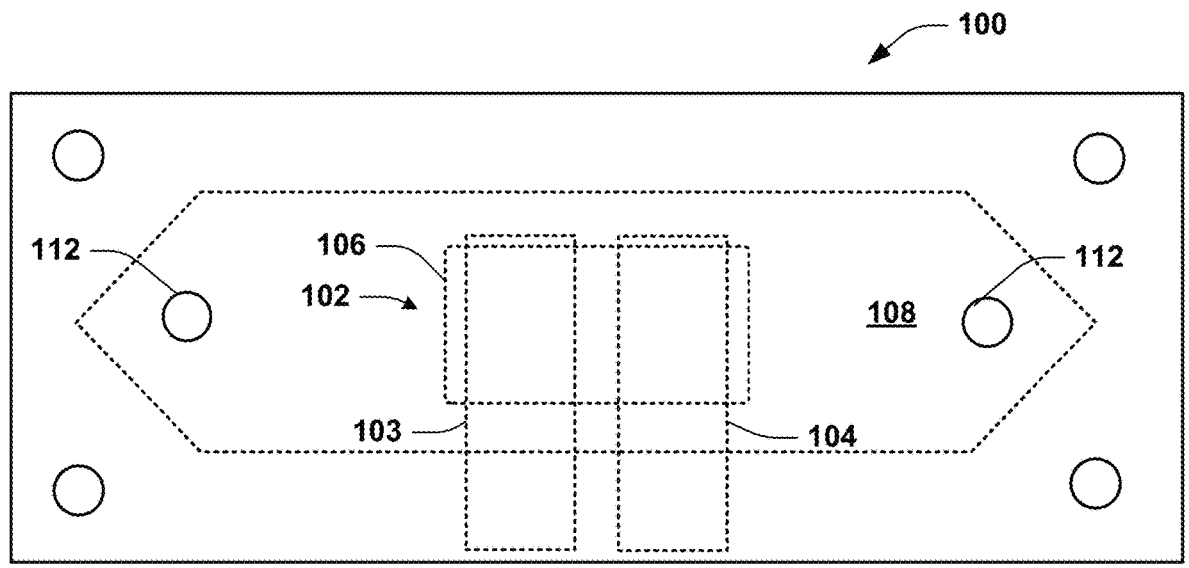
FIG. 5 depicts an example of another dielectric microsensor.

As a further example, FIG. 4 illustrates an example of the sensor fabrication and assembly that can be employed to produce the sensing apparatus 60 of FIG. 2 and the sensor 100 of FIG. 5. For purposes of clarity, the discussion of FIG. 4 uses the same reference numbers as in FIGS. 2 and 3.

As an example, the substrate layers for the top and bottom parts 84 and 86 can be fabricated using poly(methyl methacrylate) (PMMA). The intermediate channel substrate layer 88 can be formed of a thin film layer of double-sided-adhesive (DSA) material having a thickness that is much less than the electrode-containing substrate top and bottom parts 84 and 86. As one example, each of the layers 84 and 86 may be about 1.5 mm thick, whereas the layer 88 is about 250 µm thick. Other relative thicknesses can be utilized according to application requirements.

Each of the floating electrode 76 and sensing electrodes 78 and 80 can be formed by deposition of electrically conductive material deposited at a desired location (e.g., aligned with the sensing electrodes and within the channel 70) on the respective opposing surfaces of substrate layers 86 and 88. For instance, the floating electrode 106 can be an electrically conductive material (e.g., gold, copper or aluminum) deposited on the inner top surface of the cap by sputter deposition using a shadow mask and lift-off process. As an example, 100-Å/1,000-Å Cr/Au layer is evaporated on the channel surface of the substrate to form respective sensing electrodes 78 and 80. Similarly, the floating electrode 76 can be deposited on the surface of the layer 86 by evaporating a 1,000-Å Au layer and patterning with lift-off.

As shown in FIG. 4, to facilitate construction of the sensing apparatus 100, each of the layers 84, 86 and 88 can include a plurality of alignment holes 90. Each of the layers can be connected together and held in place by corresponding alignment pins 92 that can be inserted into the holes 90. In some examples, a thin film coating of a barrier material can be deposited on the surfaces of the layers 84, 86 and 88 to protect the metal and plastic surfaces from direct contact with the SUT. In other examples, such as for blood SUT, no coating may be used to help increase sensitivity.

In some examples, microfluidic inlet/outlet holes 72 in the layer 84 can be configured with a diameter to fit a standard micropipette tip or a syringe containing a volume of the sample. As one example, the microfluidic channel 70 has a total sample volume of less than about 10 µL (e.g., about 5-9 µL) and a volume of less than about 1 µL (e.g., about 0.8 µL or less) in the sensing area over the floating electrode 76. Other volumes for the channel and sensing area can be implemented according to application requirements. The microsensor 60 can be assembled by attaching the substrate layers 84 and 86 together using the DSA film layer 88 interposed therebetween. As mentioned, the alignment holes 90 and pins 92 can be used to align the floating electrode over the sensing electrodes within the microfluidic channel.

As show in the example of FIG. 4, electrical connections to the sensing electrodes 78 and 80 may be made through contact openings 94 in opposed side edges of the substrate layer 86, which can be electrically connected to the sensor interface system (e.g., to transmitter 22 and receiver 24 of interface 14). Thus connectors (e.g., pins) from associated circuitry of a connector interface (e.g., of sensing apparatus 12) can extend into the openings 94 to contact the respective electrodes 78 and 80 when the microsensor 60 is connected to the monitoring apparatus, for example.

In the example of FIGS. 2-4, the sensor 60 is demonstrated along with its terminals that can be electrically connected to interface electronics on a printed-circuit board (PCB). In some examples, the connection between the microsensor 60 and interface system 14 can be configured as a plug-and-play-type modular connection between the sensor contact pads and PCB input/output pads (e.g., using spring-loaded contact pins to provide an electrical connection). The connection method facilitates DS measurements with potentially hazardous or contaminating solutions, since the low-cost sensor (e.g., a cartridge) can be replaced after a measurement has been made for a given SUT without contaminating the entire instrument. That is, in some examples, the microsensor 60 is intended for single use, which can be discarded and replaced after each use, while the interface system 14 and associated electronics can be re-used over and over again. In other examples, a given sensor can be repeatedly reused for a plurality of measurements with the same or different SUTs.

FIG. 5 demonstrates another example of a dielectric microsensor 100 (e.g., corresponding to apparatus 12) that can be utilized in the system 10. The apparatus 100 includes a three-dimensional, parallel-plate, capacitive sensing structure 102. The capacitive sensing structure 102 includes two planar sensing electrodes 103 and 104 that are spaced apart and are separated from a floating electrode 106 according to a height of a microfluidic channel 108 to form a 3D capacitive sensing area disposed within the microfluidic chamber. The capacitive sensing structure 102 is disposed within a substrate material 110. The sensing apparatus 100 includes ports 112 (e.g., inlet and outlet holes) through which a volume of fluid (e.g., liquid or gas) can be introduced. In an example, the SUT can be a volume of blood.

A cross sectional view of the sensing apparatus 100 would be the same as shown in the example of FIG. 3, and reference may be made back to FIG. 3 and its discussion for an understanding of how different portions are constructed and attached together resulting in the sensing apparatus. In the example FIG. 5, the sensing electrodes are formed of parallel electrodes that extend from a common side edge of a corresponding substrate layer (instead of from opposed side edges as in the example FIG. 2). Other configurations may be used for the sensing apparatus 12, such as example embodiments disclosed in U.S. Patent Publication No. 2015/0346131, which is incorporated herein by reference.

Applying the sensing apparatus 100 in the context of the system 10, an input RF signal (e.g., sweeping over one or more frequency bands) can be applied (e.g., by transmitter 22) to an input electrode 103 for exciting the sensing circuit. A resulting RF output signal can be measured at the other sensing electrode 104 (e.g., by receiver 24). The measured signal can be filtered and amplified (e.g., by analog and/or digital circuitry of receiver 24) and processed (e.g., by methods/functions executed by computing device 26) to calculate permittivity for the SUT that resides within the channel 108. As disclosed herein, the data processing can be implemented to accurately measure real and/or imaginary parts of the complex relative permittivity over one or more predetermined frequencies or frequency bands. As an example, the real part of dielectric permittivity computed over one or more time intervals can be used to determine a quantitative measure of platelets (e.g., platelet count), such as disclosed herein, for a volume of blood sample. One or more other qualitative properties of the blood sample may be determined in other examples.

Figure 6:
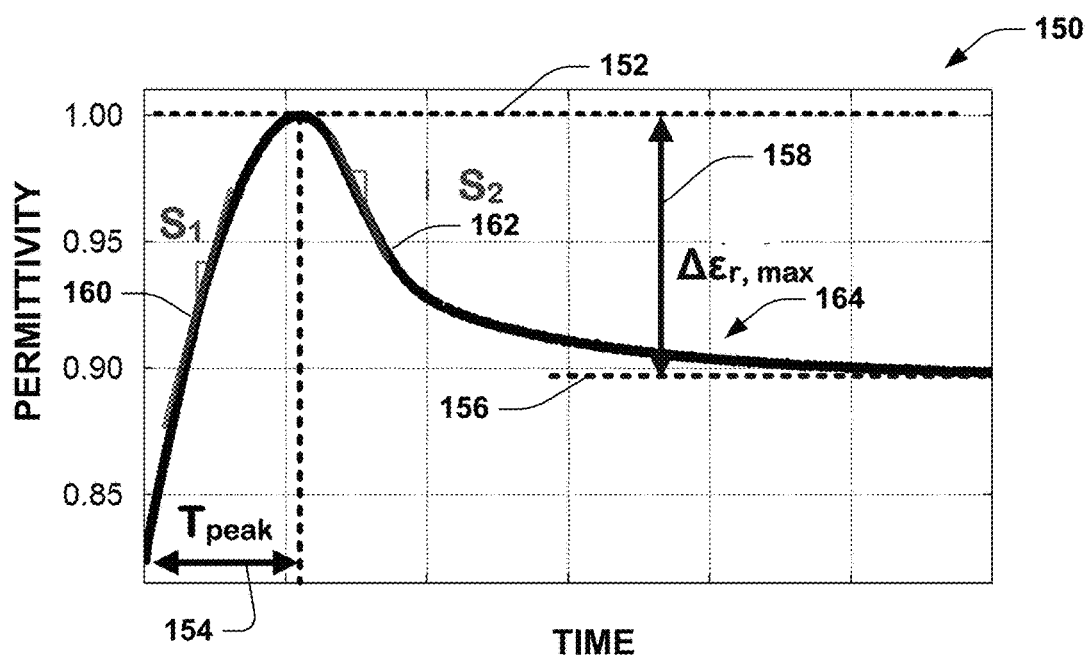
FIG. 6 depicts an example of normalized permittivity as a function of time demonstrating examples of permittivity parameters.

FIG. 6 depicts an example graph 150 of normalized permittivity as a function of time demonstrating examples of permittivity parameters that can be determined (e.g., by permittivity analyzer 46) for a given SUT based on permittivity values over a measurement time interval. In the illustrated example, the measurement data and permittivity values are normalized to the peak permittivity value 152 that occurs at time $T_{PEAK}$, demonstrated at 154. In the example graph 150, the following permittivity parameters are shown: the time of peak permittivity ($T_{PEAK}$), at 154, the initial slope (S1), at 160, the slope of permittivity decline after $T_{PEAK}$ (S2), at 162, and the magnitude of the permittivity change after $T_{PEAK}$ ($\Delta\varepsilon_{r,max}$), at 158. In other examples, other permittivity parameters could be determined from analysis of the permittivity values (e.g., performed by permittivity analyzer 46), such as associated with the tail portion of the permittivity values at the end portion of the measurement interval. Each of the permittivity parameters determined from the permittivity values in the graph 150 thus may provide an indication to quantify properties of a given SUT based on the DS measurements.

For the example of a blood SUT, some properties may include cellular properties (e.g., hemostatic properties, such as platelet function or defects in platelet function based on $\Delta\varepsilon_{r,max}$ 158) and/or molecular properties (e.g., coagulation factor based on $T_{PEAK}$) of the blood SUT. For example, the computing device of the measurement system can compute an indication of platelet count based on the computed dielectric permittivity. As disclosed herein, the dielectric permittivity can include real and imaginary components. In an example, the indication of platelet count may be determined based on the real component of dielectric permittivity (e.g., $\Delta\varepsilon_{r,max}$). The computing device thus may determine platelet-count-related changes in hemostatic properties from the computed dielectric permittivity.

Figure 7:
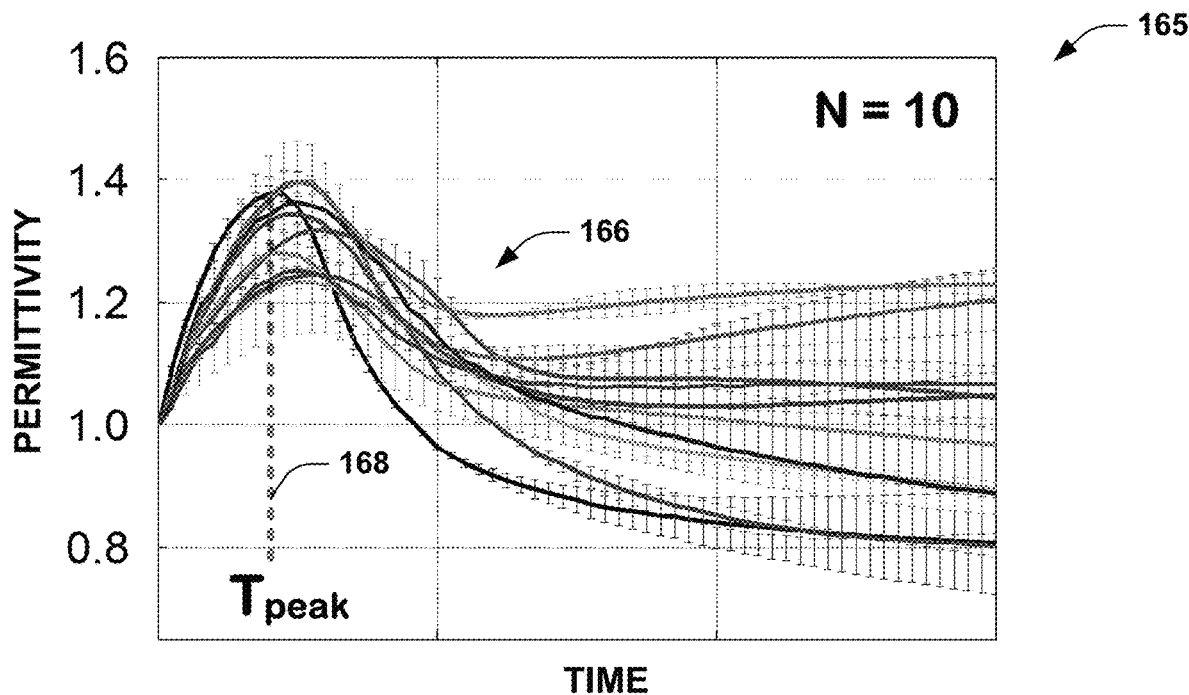
FIG. 7 is a plot of dielectric permittivity as a function of time for plurality of different samples.

FIG. 7 depicts a plot 165 of dielectric permittivity as a function of time for plurality of different blood SUTs, demonstrated at 166. In the example of FIG. 7, the plotted permittivity values of respective measurements intervals demonstrates that the approach disclosed herein yields reproducible results in relation to a time-to-peak ($T_{PEAK}$) parameter, demonstrated at 168. In this example, the plot is normalized to a first measurement point as the permittivity is taken at 1 MHz.

Figure 8:
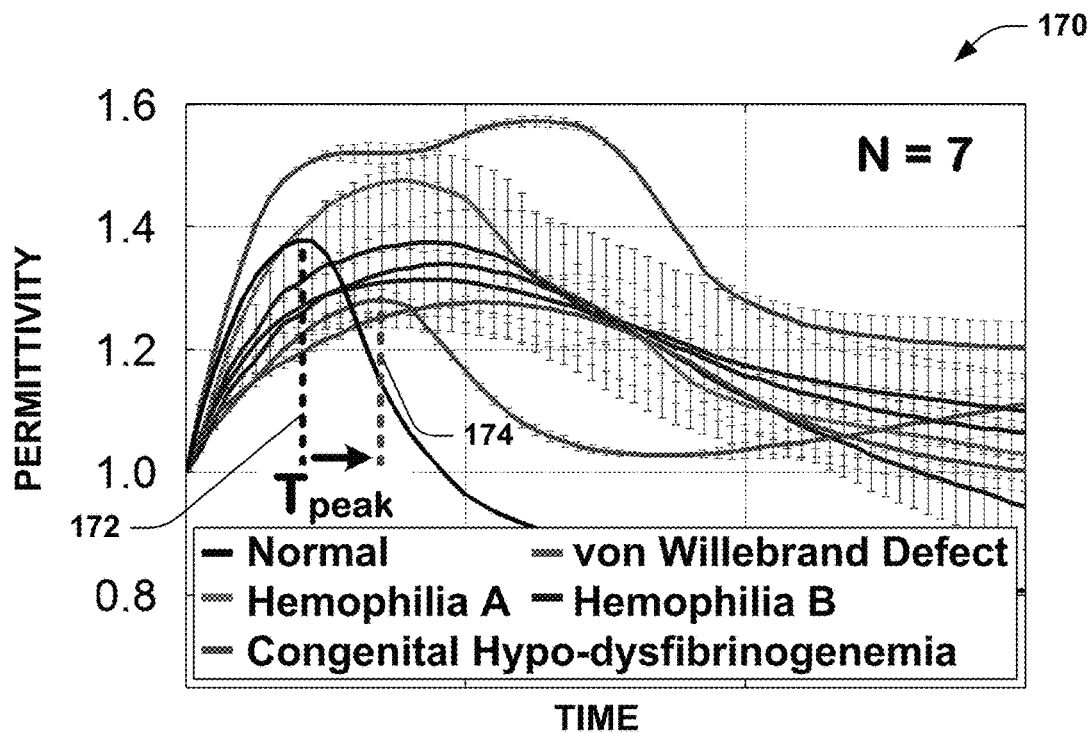
FIG. 8 depicts an example of dielectric permittivity for a plurality of samples exhibiting different coagulation properties.

FIG. 8 depicts an example plot 170 of dielectric permittivity for a plurality of different blood SUTs exhibiting different coagulation properties. In the example plot 170, the permittivity values represent blood SUTs from patients with coagulopathy, with different samples exhibiting different times to reach a peak ($T_{PEAK}$). In this example plot 170, permittivity is normalized to a first measurement point as the permittivity is taken at 1 MHz.

FIGS. 7 and 8 show that the sensor apparatus and its use according to systems and methods disclosed herein are capable of capturing various properties associated with the hemostatic process, including platelet activation and adhesion, coagulation factor assembly and thrombin generation, and fibrin formation. In an example, the real component of the computed dielectric permittivity may correlate to a measure of platelet count in the volume of blood sample. By way of comparison, the time to reach a peak ($T_{PEAK}$) in the plots of FIGS. 7 and 8 showed a statistically significant difference between the normal blood SUTs of FIG. 7 relative to the coagulopathy SUTs of FIG. 8. The approach disclosed herein further is believed to exhibit improved sensitivity as compared to conventional screening coagulation assays, such as including activated partial thromboplastin time (aPTT) and prothrombin time (PT).

Figure 9:
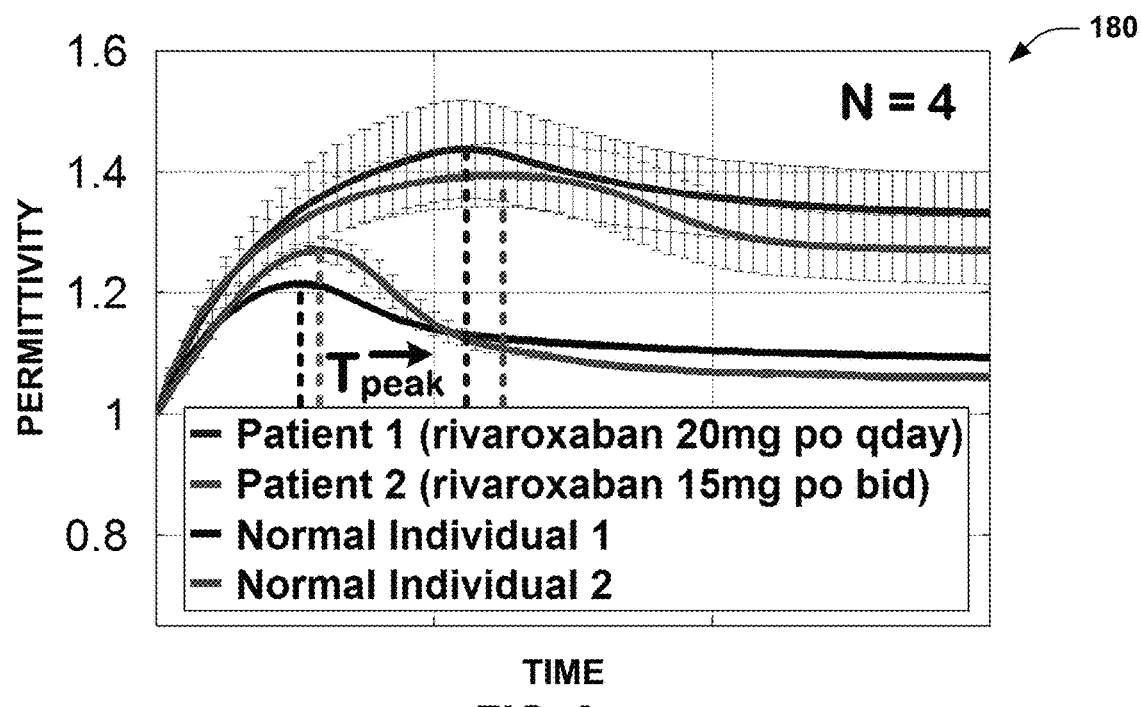
FIG. 9 depicts another example of dielectric permittivity as a function of time showing a comparison between blood samples.

FIG. 9 depicts a graph 180 showing another example of dielectric permittivity as a function of time showing a comparison between blood samples. In FIG. 9, the plot is normalized to a first measurement point as the permittivity is taken at 1 MHz. The example plot 180 of FIG. 9 demonstrates that the sensing apparatus and related systems and methods disclosed herein can provide a quantitative indication for the efficacy of target-specific oral anticoagulants (TSOACs). For example, the permittivity values for the plots in FIG. 9 show that patients on TSOACs exhibit a prolonged $T_{PEAK}$ for rivaroxaban-treated SUT. Error bars shown in FIG. 9 indicate duplicate measurements and are presented as mean±standard error of the mean (SEM).

Figure 10:
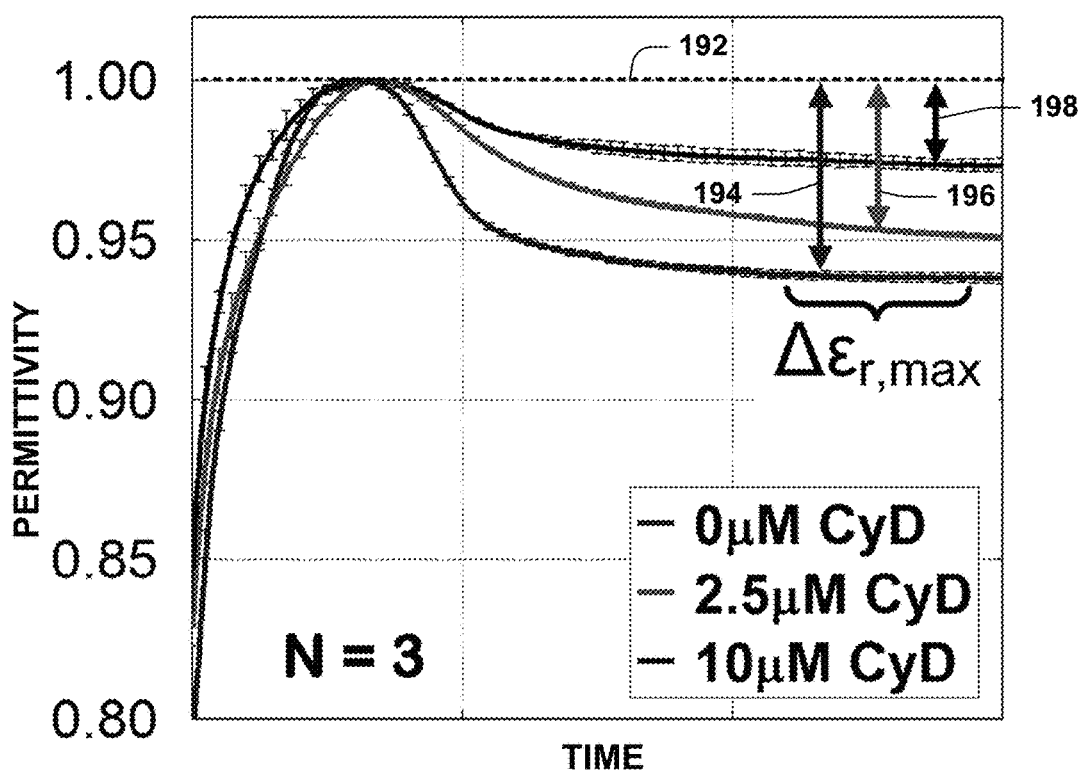
FIG. 10 depicts an example of dielectric permittivity as a function of time demonstrating different platelet function properties for a plurality of samples.

FIG. 10 depicts another plot 190 showing an example of dielectric permittivity as a function of time demonstrating different platelet function properties for a plurality of samples. For example, SUTs treated with cytochalasin D (CyD) exhibited a decrease in the difference between the peak permittivity and plateau permittivity values (i.e., $\Delta\varepsilon_{r,max}$ parameter), demonstrated at 194, 196 and 198, which indicate a sensitivity to platelet function inhibition. Error bars in the graph 190 indicate duplicate measurements and are presented as mean±SEM. In the example of FIG. 10, the permittivity values shown for each CyD-treated SUT are normalized to the permittivity at $T_{PEAK}$ demonstrated at 192 for an excitation frequency at about 1 MHz.

Figure 11A:
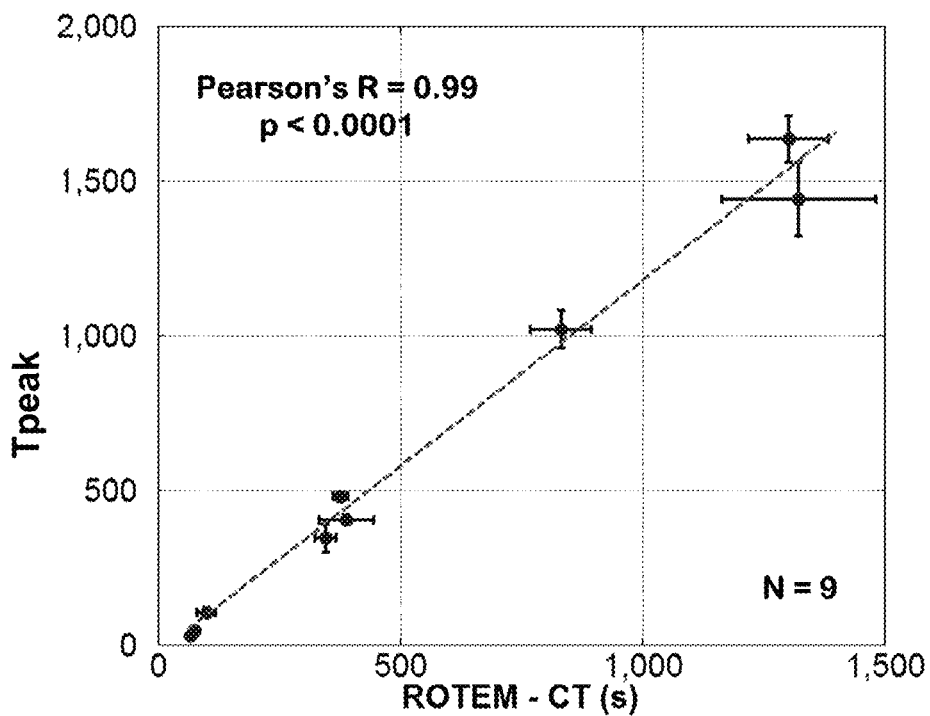
FIGS. 11A and 11B demonstrate examples of permittivity parameters correlated with respect to rotational thromboelastometry.
Figure 11B:
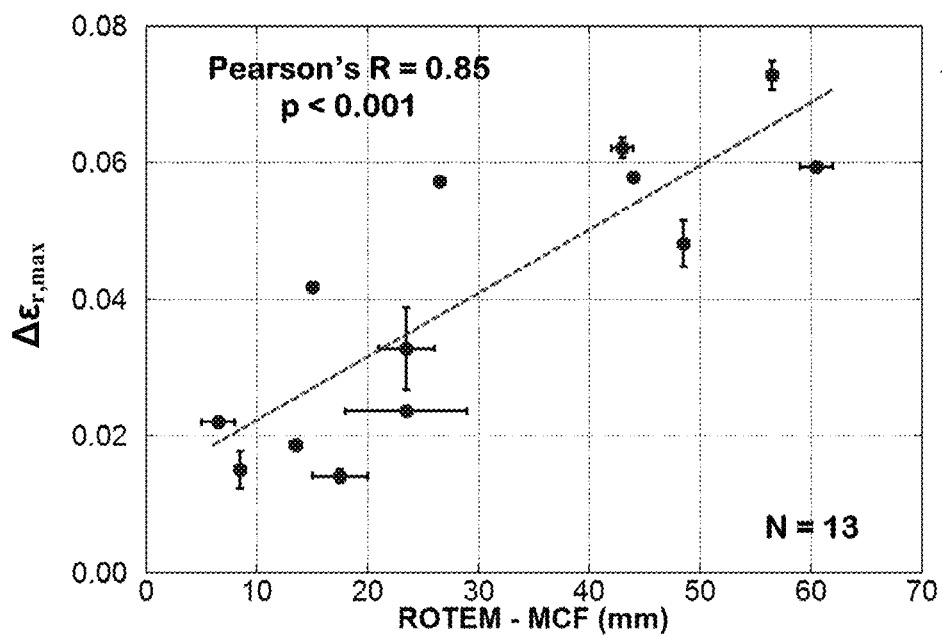

FIGS. 11A and 11B demonstrate example plots 200 and 210 showing permittivity parameters, which have been determined by the sensing apparatus and related systems and methods disclosed herein, correlated with respect to rotational thromboelastometry (ROTEM) parameters. The correlation information shown in plot 200 of FIG. 11A was derived from whole blood samples from healthy donors mixed at various concentrations of thrombin and anti-thrombin to modulate the ROTEM clotting time (CT) parameter of the prepared samples. Anti-thrombin has inhibitory effect and thrombin has accelerating effect on the final common pathway of coagulation (i.e., fibrin generation/cross-linking), prolonging and hastening, respectively, the clotting time in ROTEM measurements. In FIG. 11A, the $T_{PEAK}$ parameter determined according to the approach disclosed herein showed very strong correlation to ROTEM CT parameter.

For the example plot 210 in FIG. 11B, whole blood samples were mixed with various concentrations of CyD to modulate platelet activity, which in turn affects the maximum clot firmness, MCF, parameter in ROTEM measurements. In FIG. 11B, the $\Delta\varepsilon_{r,max}$ parameter determined from DS measurements, according to the approach disclosed herein, demonstrates strong correlation to ROTEM MCF parameter. Error bars in FIGS. 11A and 11B indicate duplicate measurements and are presented as mean±SEM.

The sensing apparatus and monitoring system disclosed herein are sensitive to a wide range of hemostatic defects arising from cellular (i.e., platelet) as well as molecular (i.e., coagulation factor) components of clotting, and has promising correlative sensitivity when compared to clinically relevant diagnostic parameters of ROTEM. For example, the computed dielectric permittivity can be used to determine an indication of platelet count, such as may be an absolute quantity or a concentration of platelets for a given blood SUT. In some examples, the computing device may calculate dielectric permittivity for the given blood sample and provide a quantitative measure of platelets or other hemostatic properties, such as platelet function or defects thereof (e.g., clot firmness or clot stability).

Figure 12:
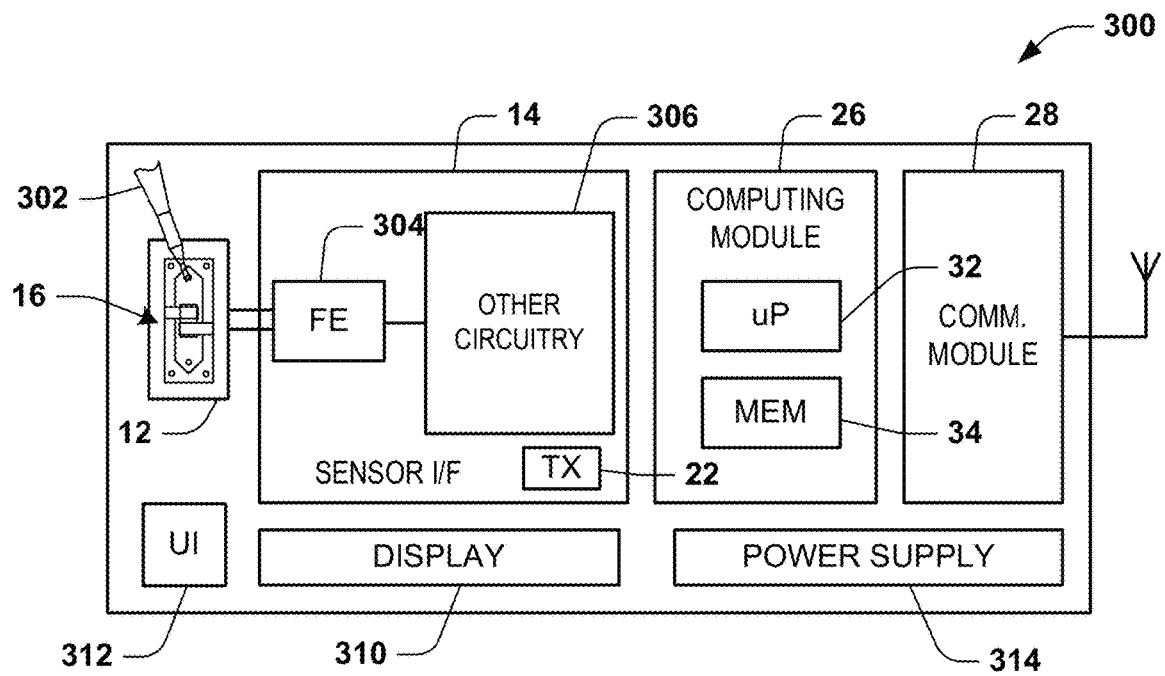
FIG. 12 depicts an example of a portable sample monitoring apparatus.

As a further example, FIG. 12 depicts another example of a DS microsensor system 300 that can be implemented as an integrated handheld system (e.g., the system 10), which can utilize plug-and-play sensors (e.g., sensor 16, 60 or 100). The components of the DS system 300 can be constructed of biocompatible materials, such as including gold, glass and PMMA, commonly used in biomicrofluidic devices.

Figure 14:
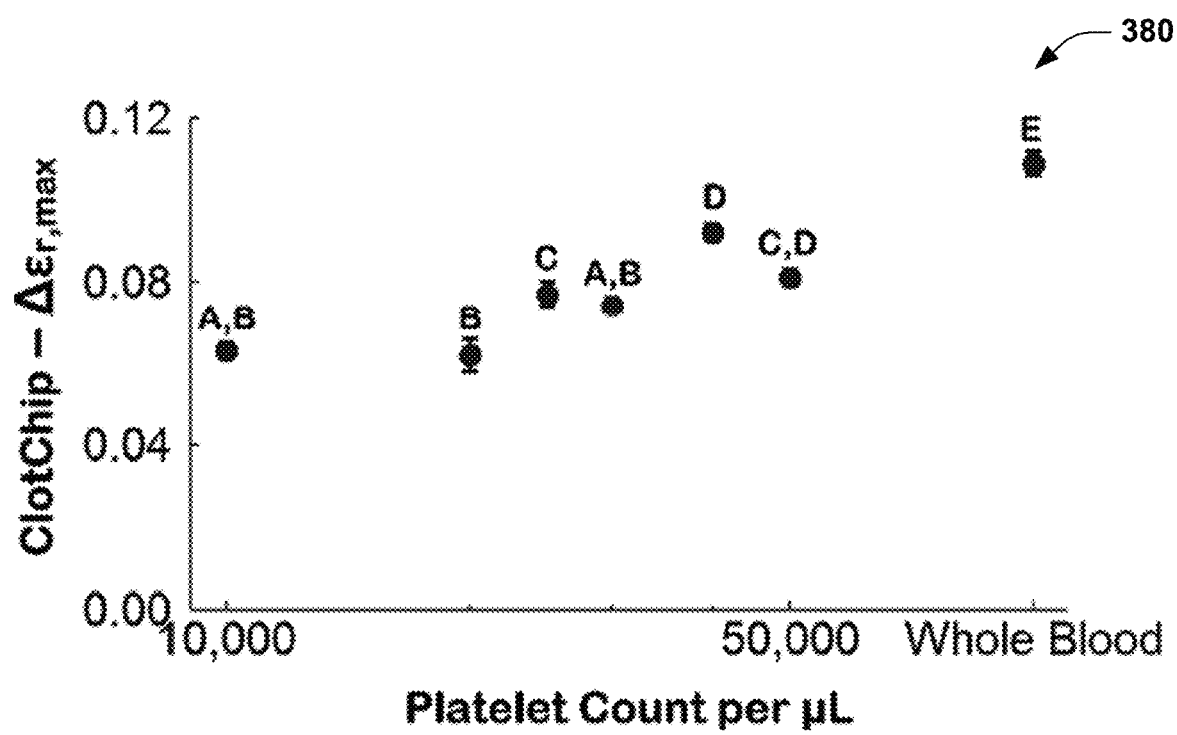
FIG. 14 is a graph demonstrating examples of permittivity parameters correlated with respect to platelet count.

In the following description of FIG. 12, for sake of clarity, components of the system 300 are referred to using similar reference numbers refer to components previously introduced with respect to FIG. 1. The system 300 can include a sensing apparatus 12 and associated interface electronics 14. In the example of FIG. 14, the sensing apparatus 12 includes a dielectric sensor 16 (e.g., corresponding to the example sensor 60 or 100). Thus, the sensor 16 and interface electronics 14 can be configured to produce a complex output that depends on (e.g., varies as a mathematical function of) the complex permittivity of the SUT disposed in a microfluidic sensor chamber of the sensor 16 in response to an excitation signal.

As an example, a micropipette (or other device, such as a syringe or the like) 302 can be employed to inject a SUT into the microfluidic chamber of the sensor 16. The sensor interface electronics 14 includes transmitter circuitry 22 to provide an excitation signal (e.g., at single frequency or frequency range of one or more frequency bands) to an input of a given sensor containing a volume of the SUT. The output of sensor 16 is coupled to respective front-end RF modules 304 (demonstrated at FE) of a receiver (e.g., receiver 24). Each front-end RF module 304 is configured to preprocess (e.g., perform down-conversion, filtering and amplification) each transmitted signal received in response to an excitation signal and provide corresponding IF signals. The IF signals from a given one of the front-end RF module 304 can be selectively provided to other receiver circuitry 306 for further processing, such as including conversion to a digital version of the signal and provided to computing module 26. The computing module 26 can calculate permittivity for the SUT based on the system output signal to provide corresponding output permittivity values stored in memory 34 as permittivity data. The permittivity data can include complex permittivity values (e.g., real and imaginary permittivity) computed over the aggregate range of excitation frequencies, including different subranges provided to the sensor 16. Permittivity data can also include raw signal measurements and the input excitation frequencies. The computing module 26 can also analyze the permittivity data to determine permittivity parameters of the SUT, such as disclosed herein, which can be used to provide an indication of properties of the SUT. One or more permittivity parameters and/or properties of the SUT may be rendered on a display 310. The system 300 may include a user interface (UI) 312 that provide a human-machine interface to enable user interaction with the system 300, such as to review results, reset the system or perform other human-machine interactions.

The computing module 26 can further provide the permittivity data and analysis thereof to a communication module 28. The communication module 28 can send the output data and raw measurement data to a remote system. For example, the communication module 28 can transmit the output data to a back office system (e.g., a server) that can be programmed to analyze the data and store the results and raw data in a database. The remote system can also communicate command information to the system 300 to program one or more of the system parameters (e.g., signal gain and/or frequency range) to control its operation and/or provide instructions to the user, such as disclosed herein. The system 300 of FIG. 12 can include a housing that contains the sensor interface electronics 14, computing module 26 and communication module 28 such that it can provide a portable, handheld device. The system 300 may also include a power supply 314, such as an internal battery and or a power interface to connect to an external supply.

While the example system of FIG. 12 is in the context of a handheld device, in other examples, the system 300 may be implemented as a bench top system. In this example, the system 300 may be configured to measure dielectric permittivity of a plurality of dielectric sensors 16, each having a respective SUT. Each sensor can include or share corresponding interface to provide respective measurement data to the computing module 26 for computing permittivity values for each of the respective SUTs. In this way a laboratory or other provider can monitor a plurality of samples concurrently.

Figure 13:
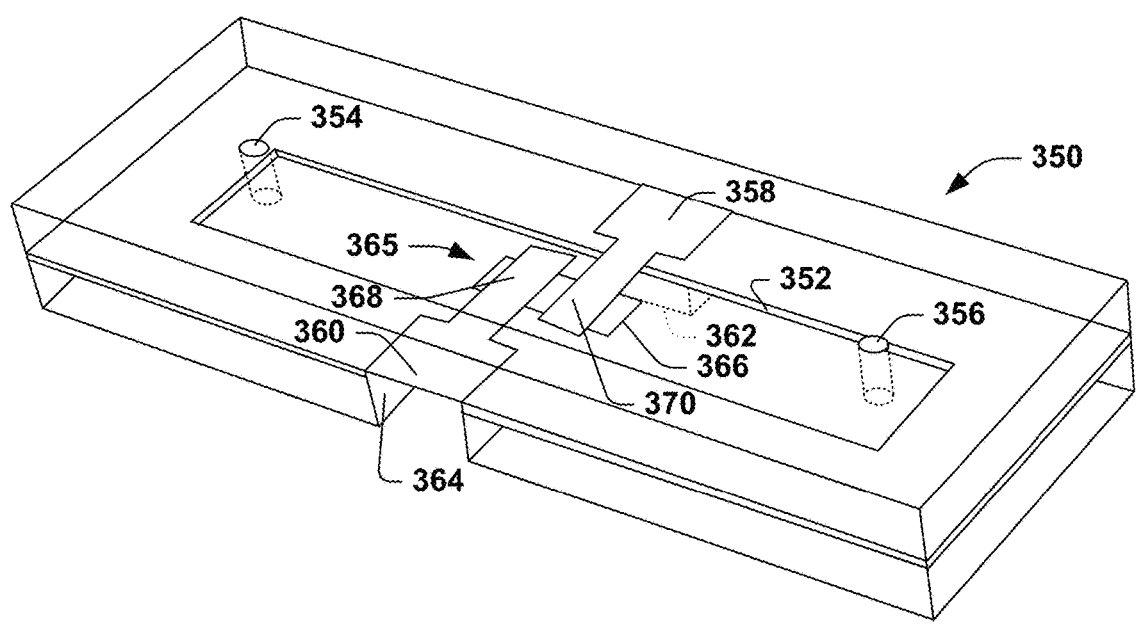
FIG. 13 depicts another example of a dielectric microsensor.

FIG. 13 depicts another example of a DS microsensor 350, which may be used in the system 10 or 300. The microsensor 350 is in the form of a rectangular prism; although other shapes could be used in other examples. The sensor 350 may be similarly constructed as other examples herein. The sensor 350 includes an interior chamber (e.g., a channel) 352 configured to hold a volume of fluid, such as blood or other SUT. One or more ports 354 and 356 provide openings into the chamber, either of which may be used to introduce the SUT into the chamber. For example, one port may be an input and the other an output port. The sensor 350 can be electrically coupled to a sensor interface system (e.g., interface 14), such as via electrical contacts 358 and 360. Other types of connections (e.g., electrically conductive or wireless) could also be utilized to provide for bi-directional communication with respect to the sensor 350. In this example, each of the contacts include a contact portion located on an opposite side of the sensor body (e.g., near the center of the chamber. A receptacle 362, 364 is formed along a surface to provide access to a contact surface of each of the respective contacts 358, 360. In this way, each receptacle 362, 364 is adapted to receive mating contacts (not shown) of the corresponding interface and thereby electrically connect with the exposed contact surface thereof. The receptacles 358, 360 also help hold the sensor in proper place during testing, such as may be enforced by providing different size and/or configuration of each of the receptacles.

The sensor 350 includes circuitry having a complex admittance (e.g., capacitance) that varies as a function of dielectric permittivity of an SUT within a fluid channel 352, such as disclosed herein. For example, one contact 358 may be an RF input to receive an RF input signal and the other contact 360 may be an RF output to provide an RF output signal. The RF output signal varies as a function of time based on the input frequency of the input signal and the dielectric permittivity of the SUT.

In this example, the sensor 350 includes a capacitive sensor 365 disposed within the fluid channel 352. For example, the capacitive sensor 365 includes a floating electrode 366 spaced apart from and opposing sensing electrodes 368 and 370 within the fluid channel 352 to provide a volumetric sensing area (e.g., corresponding to the area of overlap between the floating electrode and associated sensing electrodes). In this example, the sensing electrodes 368 and 370 are formed of longitudinally extending portions of the respective contacts, which may be coplanar with each other spaced apart and parallel to the floating electrode 366 by a distance, such as corresponding to the height of the chamber. The electrode portions 368, 370 and respective contact portions 360, 358 may be monolithic structures, for example, fabricated by disposing (e.g., screen-printing) a layer of electrically conductive material onto PMMA plastic surfaces. The capacitance of the sensor 365 is based on permittivity of material (or the absence) in the space between electrodes 366, 368 and 370. The sensing electrodes 368 and 370 can be electrically isolated from each other.

The RF input signal is electrically coupled to the input sensing electrode 370 for excitation of the capacitive sensor 365 and the other sensing electrode 368 is coupled to provide $RF_{OUT}$. Dielectric permittivity may be calculated based on the RF output signal over time. For example, dielectric permittivity may be used to compute one or more hemostatic properties, such as an indication of platelet count or other properties disclosed herein. In an example, the sensor 350 integrates dielectric spectroscopy (DS) function into a microfluidic channel as a single-use disposable cartridge.

FIG. 14 is a graph 380 demonstrating examples of permittivity parameters correlated with respect to platelet count for blood SUTs. For example, a measure of temporal variation in the real part of relative dielectric permittivity at 1 MHz was computed, and as shown, a decrease in platelet count resulted in a corresponding decrease of the $\Delta\varepsilon_{r,max}$ parameter. FIG. 14 shows the $\Delta\varepsilon_{r,max}$ parameter recorded for samples with final platelet count of 10,000, 20,000, 25,000, 30,000, 40,000, and 50,000 per μL of blood alongside that for un-modulated whole blood. Correlations between the $\Delta\varepsilon_{r,max}$ parameter and platelet count may be confirmed with ROTEM MCF measurements such that the measure of temporal variation can be used to determine the platelet count as one or more other hemostatic properties of the blood sample.

Figure 15:
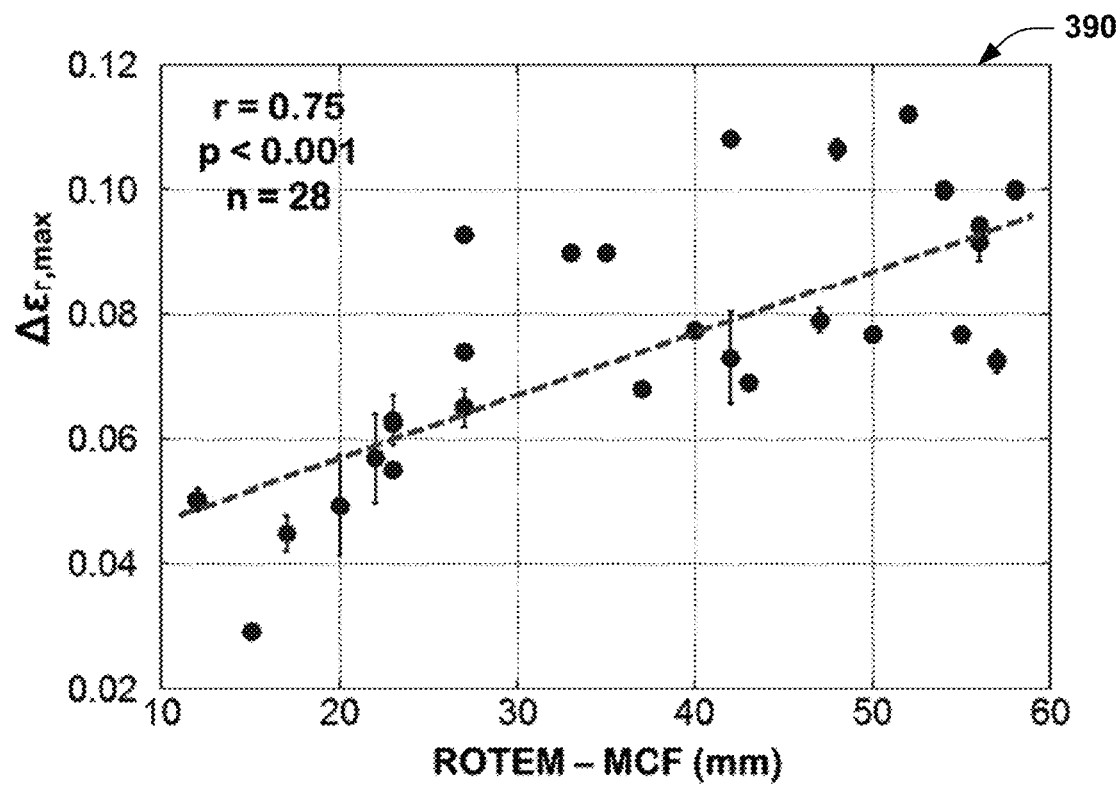
FIG. 15 is a graph demonstrating examples of permittivity parameters correlated with respect to rotational thromboelastometry.

FIG. 15 is a graph 390 demonstrating examples of permittivity parameters correlated with respect to rotational thromboelastometry. In this example, the $\Delta\varepsilon_{r,max}$ parameter exhibits a strong positive correlation ($r=0.75$, $p<0.001$, $n=28$) to the ROTEM MCF parameter, known to correlate to platelet count. Analysis of the $\Delta\varepsilon_{r,max}$ parameter further demonstrates sensitivity toward both the time of coagulation onset and clot stability. In addition to a shift in $\Delta\varepsilon_{r,max}$ parameter, a statistically significant ($p<0.05$, $n=5$) change in Tpeak was also observed upon testing platelet-rich plasma (PRP) and platelet-free plasma (PFP) samples (supplemented with RBCs at a hematocrit level of 0.5).

Figure 16:
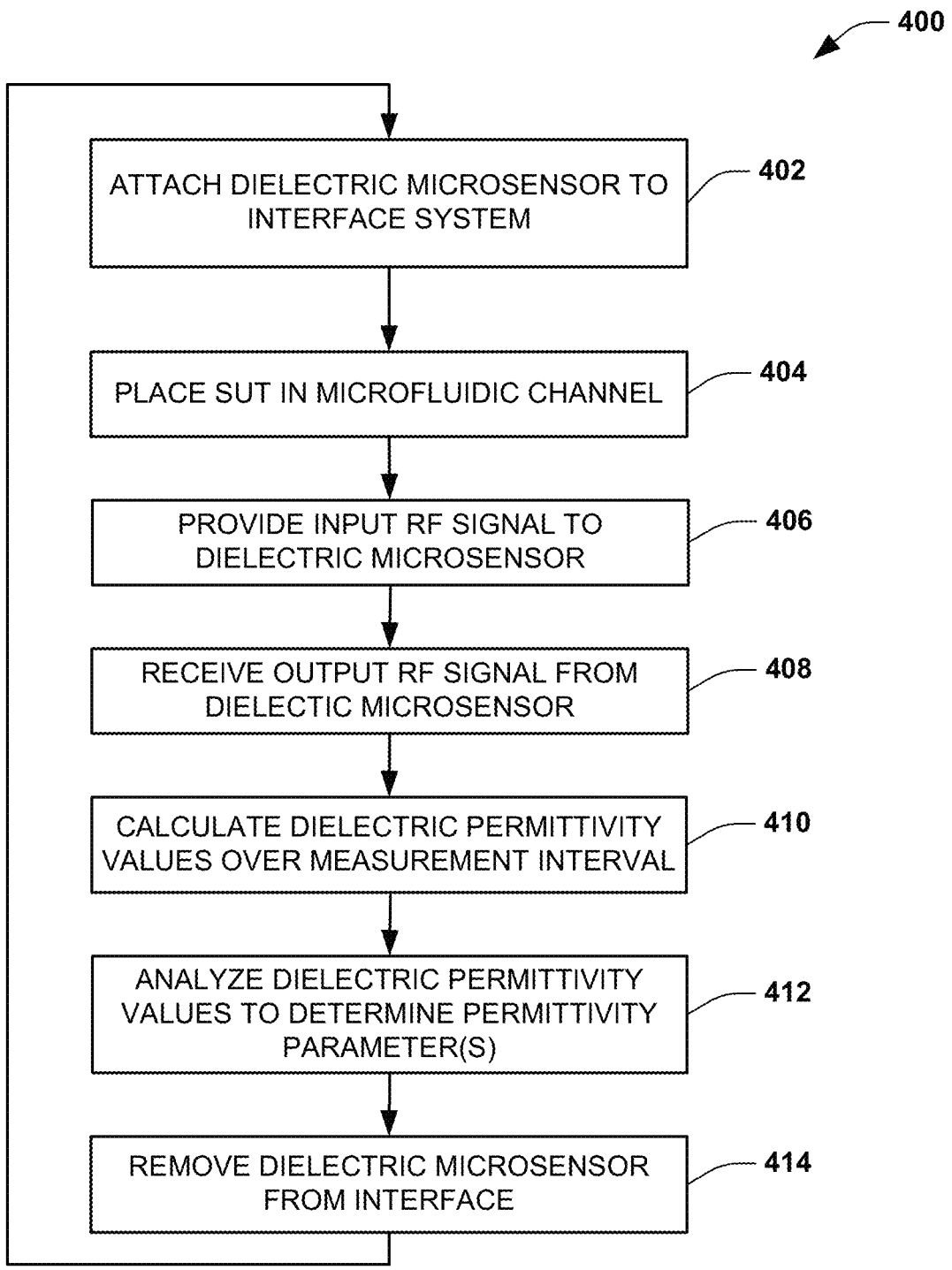
FIG. 16 is a flow diagram depicting an example of a method dielectric permittivity to determine properties of a sample under test.

FIG. 16 is a flow diagram depicting an example of a method 400 to measure dielectric permittivity and determine properties of an SUT, such as a blood sample. The method begins at 402 by attaching a dielectric microsensor (e.g., sensor 16) to an interface system (e.g., interface 14). For example, the dielectric microsensor includes a capacitive sensing structure integrated into a microfluidic channel (e.g., channel 18) that includes a fluid input to receive a sample volume of the SUT. The attachment at 402 thus can connect a transmitter and a receiver of the interface system with respective inputs and outputs of the dielectric microsensor.

At 404, the SUT is placed within the microfluidic channel of the dielectric microsensor. Once the SUT is within the dielectric microsensor, the method proceeds to 406 and an input radio frequency (RF) signal is provided to the dielectric microsensor. For example, a transmitter (e.g., transmitter 22) of the interface system provides the RF input signal to an input of the microsensor. The RF input signal can include one or more frequencies, including a calibration frequency that is used (e.g., by permittivity calculator 44) to determine a calibration permittivity for the dielectric microsensor such as corresponding to a dielectric permittivity of an air gap, as disclosed herein.

At 408, an output RF signal is received from the dielectric microsensor in response to the input RF signal. The RF output signal represents a measure of impedance (e.g., capacitance) of the SUT disposed in the dielectric microsensor. The input and output signals can be communicated between the dielectric microsensor and the interface system over a measurement time interval, for example, a fixed time or a time that depends on the measurements.

At 410, dielectric permittivity values of the SUT are calculated over a measurement time interval based on the output RF signal. As disclosed herein, the permittivity may be computed as a relative permittivity and be normalized to a selected permittivity value (e.g., peak permittivity). For example, the calibration permittivity may also be applied to the dielectric permittivity values (e.g., dividing measured permittivity values by the calibration permittivity value) to provide relative dielectric permittivity values for the SUT. The permittivity values may be stored in memory (e.g., memory 34).

At 412, the dielectric permittivity values of the SUT are analyzed over at least a portion of the measurement time interval to determine one or more permittivity parameters for the SUT. For example, the analysis at 412 includes determining a time to reach a peak dielectric permittivity value. Where the SUT includes a blood sample, the analysis at 412 may include determining an indication of platelet count based on the computed dielectric permittivity. For example, the analysis at 412 includes calculating a difference between the peak dielectric permittivity value and a plateau permittivity value (i.e., $\Delta\varepsilon_{r,max}$), such as disclosed herein. The calculated difference may be utilized to determine an indication of platelet count for the blood sample. Additionally or alternatively, the calculated difference between the peak and plateau permittivity values may be utilized to determine an indication of a qualitative platelet function (e.g., clot stability or clot firmness) for the blood sample. The dielectric permittivity values may be analyzed to determine other parameters that may be indicative of molecular properties of the SUT, such as disclosed herein.

In some examples, the analysis at 412 can include determining an indication of an anticoagulation property of the blood sample based on the time to reach the peak dielectric permittivity value. The indication of the anticoagulation property further may represent a therapeutic effect of an anticoagulation therapy, such as a target-specific oral anticoagulant.

After the measurement time interval is complete, the method proceeds to 414 and the dielectric microsensor may be removed from an interface system. Another dielectric microsensor may be attached and the method 400 repeated for analyzing properties of another SUT. In some examples, the dielectric microsensors used in performing the method 400 are disposable, single use devices that can be attached to the interface to enable sensing properties of the SUT and, after completing the test, removed and disposed of according to appropriate disposal procedures.

In view of the foregoing, the DS microsystem disclosed herein thus can provide a low-power, low-cost and portable instrument for rapidly extracting key information that characterizes the molecular and/or cellular properties of biological or other sample solutions in a broad frequency range using µL-sample volumes. The proposed measurement technique at the sensor level can be utilized to achieve high resolution in permittivity measurements.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims.

Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. A monitoring apparatus, comprising:
    a dielectric microsensor comprising a capacitive sensing structure integrated into a microfluidic chamber, the microfluidic chamber including a fluid input to receive a volume of a blood sample;
    a transmitter to provide an input radio frequency (RF) signal to an RF input of the dielectric microsensor;
    a receiver to receive an output RF signal from an RF output of the dielectric microsensor; and
    a computing device that computes dielectric permittivity values of the blood sample that vary over a time interval based on the output RF signal, the computing device to determine an indication of platelet count for the blood sample based on the dielectric permittivity values computed over at least a portion of the time interval.

2. The apparatus of claim 1, wherein the computing device analyzes the dielectric permittivity values to determine the permittivity parameter corresponding to a difference between a peak dielectric permittivity value and a plateau permittivity value where the permittivity value remains substantially constant over time.

3. The apparatus of claim 2, wherein the computing device analyzes the difference to determine the indication of platelet count for the blood sample.

4. The apparatus of claim 1, wherein the computing device is further to compute a measure of temporal variation in a real part of the dielectric permittivity values for the blood sample over at least the portion of the time interval, at least one hemostatic property of the blood sample being determined from the measure of temporal variation.

5. The apparatus of claim 1, wherein the computing device analyzes the dielectric permittivity values over the at least a portion of the time interval to determine a rate of change in permittivity values, corresponding to a slope of a portion of a curve representing the dielectric permittivity values over a corresponding part of the time interval.

6. The apparatus of claim 1, wherein the computing device is further configured to analyze a real part of the dielectric permittivity values to determine at least one permittivity parameter indicative of a qualitative platelet characteristic.

7. The apparatus of claim 1, wherein the transmitter provides the input RF signal to include a test signal having a frequency that includes 1 MHz.

8. The apparatus of claim 1, wherein the capacitive sensing structure comprises:
    a floating electrode disposed on surface of the microfluidic chamber;
    a pair of sensing electrodes disposed on another surface of the microfluidic chamber opposite the floating electrode to provide a capacitive sensing area within the microfluidic chamber, the input RF signal provided to one of the sensing electrodes and the output RF signal being received from another of the sensing electrodes.

9. The apparatus of claim 1, further comprising:
    a housing that contains the transmitter, the receiver and the computing device; and
    a sensor interface including electrical contacts configured to connect to the dielectric microsensor for communicating the RF input signal and the RF output signal.

10. A method, comprising:
    providing an input radio frequency (RF) signal to a dielectric microsensor that includes a blood sample under test (SUT) disposed therein;
    receiving an output RF signal from the dielectric microsensor in response to the input RF signal, the RF output signal representing a measure of impedance of the dielectric microsensor;
    calculating dielectric permittivity values of the blood sample over a measurement time interval based on the output RF signal; and
    analyzing the dielectric permittivity values of the blood sample over at least a portion of the measurement time interval to determine an indication of platelet count for the blood sample.

11. The method of claim 10, wherein analyzing the dielectric permittivity values further comprises determining a difference between a peak dielectric permittivity value and a plateau permittivity value.

12. The method of claim 11, further comprising analyzing the difference to determine the indication of platelet count for the blood sample.

13. The method of claim 10,
wherein prior to the providing and the receiving the method further comprises:
attaching the dielectric microsensor to an interface system to connect a transmitter and a receiver of the interface system with the dielectric microsensor;
placing the blood sample within a chamber of the dielectric microsensor; and
wherein after the measurement time interval the method further comprises removing the dielectric microsensor from the interface system.

14. The method of claim 10, further comprising:
providing the RF input signal at calibration frequency to determine a calibration permittivity for the dielectric microsensor; and
applying the calibration permittivity to the dielectric permittivity values to provide relative dielectric permittivity values for the blood sample.

15. The method of claim 10, further comprising analyzing the dielectric permittivity values to determine a time to reach a peak dielectric permittivity value.

16. The method of claim 15, wherein analyzing the dielectric permittivity values further comprises determining an indication of an anticoagulation property of the blood sample based on the time to reach the peak dielectric permittivity value.

17. A system, comprising:
a sensor interface comprising an input and an output, the output to connect to an input of a sensing apparatus and the input to connect to an output of the sensing apparatus, the sensing apparatus to receive a blood sample;
a transmitter to provide an input radio frequency (RF) signal to the output of the sensor interface; and
a receiver to receive an output RF signal from the input of the sensor interface in response to the input RF signal and based on an impedance of the sensor apparatus;
a computing device to compute dielectric permittivity values of the blood sample that vary over a time interval based on the output RF signal, the computing device to determine an indication of platelet count for the blood sample based on the dielectric permittivity values computed over at least a portion of the time interval.

18. The system of claim 17, wherein the computing device analyzes the dielectric permittivity values to calculate a difference between a peak dielectric permittivity value and a plateau permittivity value where the permittivity value remains substantially constant over time, the indication of platelet count for the blood sample being determined based on the difference.

19. The system of claim 17, wherein the sensing apparatus is removably connected to the input and the output of the sensor interface for communicating the RF input signal and the RF output signal with respect to the sensing apparatus, the sensing apparatus comprising a capacitive sensing structure integrated into a microfluidic chamber, the microfluidic chamber including a fluid input to receive a volume of the blood sample.

20. The system of claim 19, wherein the capacitive sensing structure comprises:
a floating electrode disposed on surface of the microfluidic chamber;
a pair of sensing electrodes disposed on another surface of the microfluidic chamber opposite the floating electrode to provide a capacitive sensing area within the microfluidic chamber, the input RF signal provided to one of the sensing electrodes and the output RF signal being received at another of the sensing electrodes.

* * * * *